US009556237B2

(12) United States Patent
Schmaljohn et al.

(10) Patent No.: US 9,556,237 B2
(45) Date of Patent: Jan. 31, 2017

(54) ANTIVIRAL RIFT VALLEY FEVER VIRUS PEPTIDES AND METHODS OF USE

(71) Applicant: The United States of America, as represented by the Secretary of the Army, Washington, DC (US)

(72) Inventors: Connie Schmaljohn, Middletown, MD (US); Robert F. Garry, New Orleans, LA (US); Jeffrey W. Koehler, Frederick, MD (US); Mary Guttieri, Bethesda, MD (US)

(73) Assignee: The United States of America, as represented by the Secretary of the Army, on behalf of the U.S. Army Medical Research Institute of Infectious Diseases, Washington, DC (US)

( * ) Notice: Subject to any disclaimer, the term of this patent is extended or adjusted under 35 U.S.C. 154(b) by 0 days.

(21) Appl. No.: 14/730,277

(22) Filed: Jun. 4, 2015

(65) Prior Publication Data

US 2015/0337015 A1 Nov. 26, 2015

Related U.S. Application Data

(63) Continuation-in-part of application No. PCT/US2013/072952, filed on Dec. 4, 2013.
(Continued)

(51) Int. Cl.
*A61K 38/10* (2006.01)
*A61K 38/16* (2006.01)
(Continued)

(52) U.S. Cl.
CPC ............. *C07K 14/005* (2013.01); *A61K 38/10* (2013.01); *A61K 38/162* (2013.01); *A61K 39/12* (2013.01); *A61K 47/48246* (2013.01); *C07K 14/175* (2013.01); *C12N 7/00* (2013.01); *A61K 38/00* (2013.01); *C12N 2760/12233* (2013.01)

(58) Field of Classification Search
CPC ...... A61K 38/10; A61K 38/162; A61K 39/12; C07K 14/175
See application file for complete search history.

(56) References Cited

U.S. PATENT DOCUMENTS

| 4,499,084 A * | 2/1985 | Dixon | A61K 9/0014 514/46 |
| 2004/0101534 A1* | 5/2004 | Diamond | A61K 39/245 424/186.1 |

(Continued)

OTHER PUBLICATIONS

Koehler et al. "A Fusion-Inhibiting Peptide against Rift Valley Fever Virus Inhibits Multiple, Diverse Viruses." PLOS Neglected Tropical Diseases. Sep. 12, 2013, vol. 7, Issue 9, pp. 1-11.*

(Continued)

*Primary Examiner* — Jeffrey E Russel
(74) *Attorney, Agent, or Firm* — Nash and Titus

(57) ABSTRACT

The invention entails synthetic short peptides based on Rift Valley Fever Virus (RVFV) fusion protein. The peptides are broad-spectrum antivirals, and are useful for prophylactic treatment against or therapeutic treatment of infection by hemorrhagic fever viruses, such as RVFV, Ebola Virus, and Andes Virus, as well as vesicular stomatitis virus.

8 Claims, 25 Drawing Sheets

Related U.S. Application Data

(60) Provisional application No. 61/733,966, filed on Dec. 6, 2012.

(51) Int. Cl.
   *C07K 14/005* (2006.01)
   *A61K 47/48* (2006.01)
   *C12N 7/00* (2006.01)
   *A61K 39/12* (2006.01)
   *C07K 14/175* (2006.01)
   *A61K 38/00* (2006.01)

(56) References Cited

U.S. PATENT DOCUMENTS

| | | | |
|---|---|---|---|
| 2006/0088909 A1* | 4/2006 | Compans | C07K 14/005 435/69.1 |
| 2009/0011000 A1* | 1/2009 | Hinz | C07K 14/005 424/450 |
| 2011/0027282 A1 | 2/2011 | Kotenko | |
| 2012/0219613 A1* | 8/2012 | Lee | C07D 417/06 424/450 |
| 2014/0212447 A1* | 7/2014 | Richt | C07K 16/10 424/186.1 |

OTHER PUBLICATIONS

Zhang et al., The EMBO Journal (2011) 30, 3854-3863.
Nguyen, 2009. A novel high-throughput cell-based method for integrated quanitification . . . Biotechnol Bioeng 103:664-75.
Letter to the Editor:A Synthetic Peptide from HIV-1 gp41 Is a Potent Inhibitor of Virus-Mediated Cell-Cell Fusion, AIDS Research & Human Retroviruses vol. 9, No. 11, 1993.
Alcami, A., 1992. A soluble receptor for interleukin-1 beta encoded by Vaccinia virus: a novel mechanism . . . Cell 71:153-67.
Kamrud,. 1999. Comparison of the protective efficacy of naked DNA, DNA-based Sindbis replicon, and packaged Sindbis replicon vectors . . . Virology 263:209-19.
Trombley, et al., Am. J. Trop. Med. Hyg., 82(5), 2010, pp. 954-960.
Malashkevich, et al., Proc. Natl. Acad. Sci. USA, vol. 96, pp. 2662-2667, Mar. 1999 Biochemistry.
Dessau et al., PNAS, Jan. 29, 2013, vol. 110, No. 5.
Roche et al., Science, vol. 313 Jul. 14, 2006.
Kilgore et al., Journal of Virology, vol. 77, No. 13, Jul. 2003, p. 7669-7672.
Hooper et al., Virology 255, 269-278 (1999).
Liao, JCB Article, The Journal of Cell Biology, vol. 171, No. 1, Oct. 10, 2005, 111-120.
Golden and Hooper, Clinical and Vaccine Immunology, vol. 17, No. 11, Nov. 2010, p. 1656-1665.
Liao et al., Journal of Virology, vol. 80, No. 22, Nov. 2006, p. 11362-11369.
Towner, et al., Virology 332 (2005) 20-27.
Battles et al., Am. J. Trop. Med. Hyg.. 39(6), 1988, pp. 617-631(8-134).
Tischler et al., Journal of General Virology (2005), 86, 2937-2947.
Sainz et al., Virus Research 120 (2006), 146-155.
Ashkenazi et al., Eur Biophys J (2011) 40:349-357.
Haller et al., Cytokine & Growth Factor Reviews 18 (2007) 425-433.
Pestka et al., Immunological Reviews 2004, vol. 202: 8-32.
Weber et al., Viral Immunology, vol. 17, No. 4, 2004, pp. 498-515.
Ank, et al., Journal of Virology, May 2006, vol. 80, No. 9. p. 4501-4509.
Vialat et al., Virus Research 52 (1997) 43-50.
Snider et al., Protein Science 2009 vol. 18:2624-2628.
Pangerl, et al., Journal of Virology, vol. 85, No. 17, Sep. 2011, p. 8495-8501.
Allison et al.,Journal of Virology, vol. 75, No. 9, May 2001, p. 4268-4275.
Ramanathan et al., Virology 374 (2008) 138-150.
Allison et al., Journal of Virology, vol. 69, No. 2, Feb. 1995. p. 695-700.
Schmidt AG, Yang PL, Harrison SC (2010) Peptide Inhibitors of Dengue-Virus Entry Target a Late-Stage Fusion Intermediate. PLoS Pathog 6(4).
Hrobowsky et al., Virology Journal 2005, 2:49.
Kilby et al., Nature Medicine, vol. 4, No. 11, Nov. 1998, pp. 1302-1307.
Garry et al., Theoretical Biology and Medicine Modelling 2004, 1:10.
Lee MS, Bondugula R, Desai V, Zavaljevski N, Yeh I-C, et al. (2009) PSPP: A Protein Structure Prediction Pipeline for Computing Clusters. PLoS ONE 4(7).
Drosten et al., Journal of Clinical Microbiology, vol. 40, No. 7, Jul. 2002, p. 2323-2330.
Lok S-M, Costin JM, Hrobowski YM, Hoffmann AR, Rowe DK, et al. (2012) Release of Dengue Virus Genome Induced by a Peptide Inhibitor. PLoS ONE 7(11).
Madani, et al., Clinical Infectious Diseases 2003; 37:1084-92.
Durand et al., Emerging Infectious Diseases • vol. 9, No. 6, Jun. 2003.
Schmidt AG, Lee K, Yang PL, Harrison SC (2012) Small-Molecule Inhibitors of Dengue-Virus Entry. PLoS Pathog 8(4).
Costin JM, Jenwitheesuk E, Lok S-M, Hunsperger E, Conrads KA, et al. (2010) Structural Optimization and De Novo Design of Dengue Virus . . . PLoS Negl Trop Dis 4(6).
Brassanelli et al., The EMBO Journal (2004) 23, 728-738.
Lee et al., Nature. Jul. 10, 2008; 454(7201): 177-182.
Roche et al., Science vol. 315, Feb. 9, 2007.
Haller et al., Virology 344 (2006) 119-130.
Xu et al., vol. 205, No. 4, Apr. 14, 2008 981-992.
Novelli et al., Cytokine & Growth Factor Reviews 15 (2004) 367-377.
Alcami et al., Journal of Virology, vol. 74, No. 23, Dec. 2000, p. 11230-11239.
Symons et al.,Cell, vol. 61, 551-560, May 19, 1995.
Colamonici et al., J. Virol., 80:4501-9 (2006).
Harrison, Nat Struct Mol Biol. Jul. 2008 ; 15(7): 690-698.

\* cited by examiner

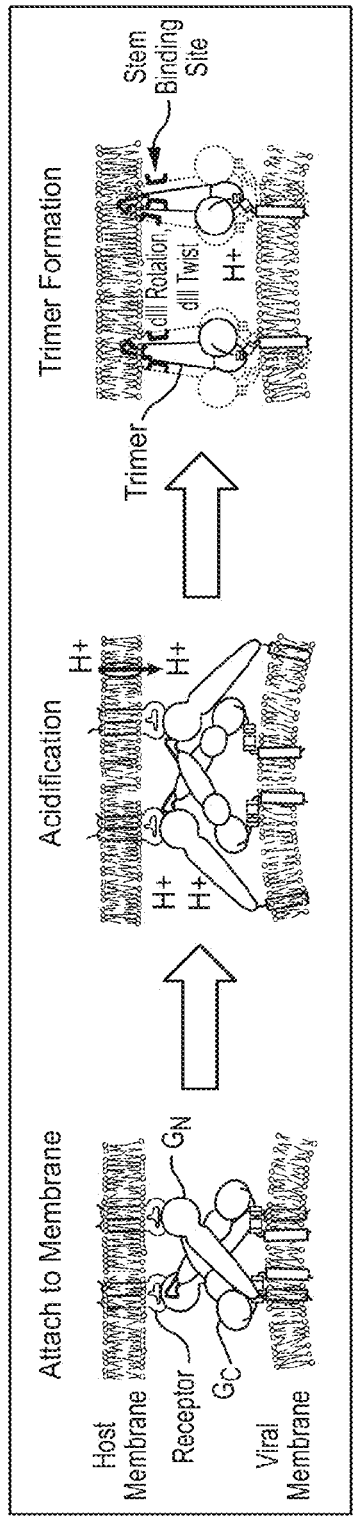

FIG. 10B

ANTIVIRAL RIFT VALLEY FEVER VIRUS PEPTIDES AND METHODS OF USE

GOVERNMENT INTEREST

The invention described herein may be manufactured, used, and licensed by or for the United States Government.

BACKGROUND OF THE INVENTION

1. Field of the Invention

The present invention relates to novel, broad-spectrum, antiviral peptides, compositions containing one or more of these, and their use for the prophylactic treatment against and/or therapeutic treatment of infection by hemorrhagic fever viruses (HFVs), such as Rift Valley fever virus (RVFV), Ebola virus (EBOV), and Andes virus (ANDV). Additionally, these peptides were capable of inhibiting vesicular stomatitis virus (VSV), an agricultural pathogen with limited therapeutic availability.

2. Background

Viral hemorrhagic fevers (VHFs) are highly infectious and often fatal. VHF viruses possess enveloped RNA genomes and emanate from four distinct families, the Arenaviridae, Bunyaviridae, Filoviridae, and Flaviviridae. Upon infection in humans, VHFs elicit a flu-like illness (e.g., fever, malaise, headache, sore throat), which can rapidly progress into a life-threatening multisystem syndrome, with mortality rates reaching as high as 95%. To date, effective countermeasures to VHFs are either unavailable or inadequate. In addition to natural outbreaks, the threat posed by these viruses is further heightened due to their potential use as bioweapons, which is substantiated by their capacity for dissemination by the aerosol route (4) (reference citations are listed at the end of this document text). Inadequate countermeasures targeted against these viruses pose a serious threat to military welfare and public health. Viral agents contributing to this threat include, for example purposes only, RVFV, EBOV and ANDV.

Rift Valley fever (RVF) is a disease of major public health and economic concern, affecting humans and livestock throughout Africa (1, 10, 11, 13, 23, 25) and the Arabian Peninsula (33). The etiological agent of this zoonosis, RVFV, is an arbovirus belonging to the *Phlebovirus* genus in the family Bunyaviridae. RVFV was first identified following an outbreak in Kenya's Rift Valley in 1931 (10). RVFV infection is severe in animals, especially sheep, cattle, and goats, resulting in high mortality rates in newborns and near 100% abortion rates in pregnant animals. In humans, infection is usually self-limiting, but a small percent of cases (1-2%) can progress to severe hepatitis with hemorrhagic manifestations. In addition, retinal inflammation can lead to permanent vision loss in about 1-10% of infected patients (23).

In addition to RVFV, other HFVs of concern to humans include ANDV, a bunyavirus, and EBOV, a filovirus. Occasional outbreaks of EBOV can lead to extremely high morbidity and mortality, and ANDV is endemic in South America. All of these are highly pathogenic biothreat agents, and currently there are no U.S. Food and Drug Administration (FDA)-approved vaccines or therapeutics against these agents licensed for human use. Additionally, VSV, which can cause a limited disease in humans (20), can cause an acute disease in pigs, horses, and cattle that usually resolves within two weeks.

RVFV, EBOV, ANDV and VSV are enveloped animal viruses, which are able to infect a target cell after (1) binding to a target cell membrane, and (2) fusing with either the plasma membrane or an internal membrane of the target cell. The fusing process is carried out by the virus fusion proteins. The envelope fusogenic proteins are comprised of at least two different classes of fusion proteins based on structural similarities. The fusion proteins of arena-, filo-, myxo-, paramyxo-, and retroviruses are collectively known as Class I fusion proteins. Features of Class I fusion proteins include a N-terminal membrane disruptive fusion peptide and a pair of extended alpha helices (15, 16, 40). The alpha-, bunya-, and flaviviruses utilize Class II fusion proteins which are characterized by predominately beta sheets and an internal fusion peptide domain. These fusion proteins contain multiple domains that interact with and disrupt bilayer membranes, a process required for virion-cell fusion (7).

Like other bunyaviruses, RVFV is an enveloped RNA virus containing three genome segments. The large (L) segment encodes the viral polymerase, the medium (M) segment the glycoproteins, Gn and Gc, and two non-structural proteins, and the small (S) segment the nucleocapsid protein, N, and the nonstructural protein NS s. RVFV entry into permissive cells is mediated by Gn and Gc, with Gc predicted to be a class II fusion protein [17] that uses a low pH-dependent fusion mechanism following endocytosis [14]. While little is known about the fusion process of RVFV, the functional aspects of other class II fusion proteins have been well characterized [18]. For example, the flavivirus fusion protein, E, binds to a cellular receptor, and the virus enters cells by endocytosis. Acidification of endocytic vesicles results in a low-pH dependent rearrangement of E, rearranging from a dimer to a trimer [3] and inserting a previously hidden fusion peptide into the target cellular membrane [26, 5, 2, 28]. A second rearrangement of the trimer pulls the viral and cellular membranes into close proximity to allow membrane disruption and fusion to occur [5]. Based on structural modeling, the hydrophobic residues of the stem region N-terminal to the transmembrane domain of E likely moves through a groove formed by domain II interactions in the E trimer during this second rearrangement; as the stem travels through this groove, domain II (with the fusion loop inserted into the endocytic membrane) is pulled toward the transmembrane domain within domain II [26]. These large conformational rearrangements that take place during this fusion process present potential opportunities to disrupt the fusion process and prevent a productive infection (18, 26).

Targeting this viral entry process with inhibitory peptides has proven successful with multiple viruses including the flavivirus dengue virus (DENV) (8, 19, 32), SARS coronavirus (31), and, most notably, HIV-1 (21, 39). The mechanism of action for various fusion inhibitors appears to differ depending on the region of the fusion protein the peptide was designed. For DENV, peptides designed to disrupt the hinge region of domain II or the beta sheet interaction between domains I and II are thought to trigger a rearrangement of the viral glycoproteins and thus interfere with virion binding to the targeted cell (8). In contrast, peptides homologous to the hydrophobic DENV stem region of the fusion protein interfere with fusion of the viral and cellular membranes (32). Data suggest that this stem peptide interferes with the movement of the viral stem region along domain II, preventing the two membranes from coming in close enough proximity to destabilize and fuse (32).

Yet another mechanism was described for HIV involving gp41 rearrangement in response to gp120 binding of CD4 and either the co-receptor CCR5 or CXCR4. This rearrangement exposes the C- and N-terminal heptad repeat domains which, following the second gp41 rearrangement, form a 6-helix bundle in the post-fusion state. Peptides analogous to the C-terminal heptad repeat bind to the exposed N-terminal heptad repeat when these domains are exposed, preventing completion of the second rearrangement and formation of the 6-helix bundle (22).

SUMMARY OF THE INVENTION

The hemorrhagic fever viruses (HFVs) of human concern include the bunyaviruses RVFV, ANDV, and the filovirus EBOV. There is a significant disease burden for RVFV, especially during epidemics, and ANDV is endemic in South America. Occasional outbreaks of EBOV can lead to significant morbidity and mortality.

There are currently no US Food and Drug Administration (FDA)-approved vaccines or therapeutics against these agents licensed for human use. While there are several vaccines being evaluated for RVFV, having FDA Investigational New Drug (IND) status, there are significant safety and efficacy concerns. Additionally, the utility of these vaccines post-exposure is undetermined in humans, so there is a significant need to develop therapeutics for this and additional HFVs.

For enveloped viruses, such as RVFV, EBOV, ANDV, and VSV, a critical step in the entry process is the fusion of the viral envelope with a cellular envelope (the plasma membrane or an internal membrane), allowing for the viral genetic material to enter the cell—in other words, such viruses need to bind to a target cell membrane and fuse with either the plasma membrane or an internal membrane of a target cell in order to inject the viral genetic material into the targeted cell. Viral fusion proteins mediate this process through a series of protein re-arrangements which disrupt the viral and cellular membranes and mediate the two membranes' fusion. This fusion process is mediated by at least three classes of fusion proteins, Class I, II, and III, based on the protein sequence and structure. For RVFV, the glycoprotein Gc (Class II fusion protein) mediates this fusion event following entry into the endocytic pathway, allowing the viral genome to enter into the cell cytoplasm. This process presents an opportunity to inhibit virus entry: if the fusion or other early entry process can be disrupted, successful infection by the virus can be inhibited.

We explored mechanisms associated with viral fusion to develop countermeasures against hemorrhagic fever viruses such as RVFV, EBOV and ANDV, as well as VSV, an agricultural pathogen. Keeping in mind two main Points—(1) that enveloped viruses require the fusion of the viral membrane and a cellular membrane for the viral genome to enter into the cell cytoplasm, and (2) that this entry is mediated by a viral fusion protein, the inventors developed six synthetic peptides based on the RVFV fusion protein—designated RVFV-5, RVFV-6, RVFV-7, RVFV-8, RVFV-9, and RVFV-10. We found that these peptides inhibit RVFV infectivity by preventing the fusion process.

The inventors designed a number of peptides to try to target RVFV's fusion protein, and six of them did in fact inhibit RVFV. A similar approach has been successful previously with the identification of inhibitory peptides for SARS-coronavirus and the flaviviruses (E.g. West Nile and Dengue viruses). We discovered further that our novel synthetic peptides exhibited broad inhibition of other viruses including EBOV (Class I fusion protein), ANDV (Class II fusion protein), and VSV (likely a Class III fusion protein). One RVFV peptide in particular, designated RVFV-6, was more effective than the others in inhibiting these virures. We demonstrated that these peptides were not toxic to the host cells. Thus, they have advantages that make them ideal for antiviral use.

By the data and description herein, we show that peptides analogous to the RVFV Gc stem region inhibit RVFV infectivity in vitro using viral inhibition assays with no toxicity to cells. We developed a plasmid-based cell:cell fusion assay and show the mechanism of action is inhibition of the fusion process. Furthermore, we show that this peptide's inhibition is not limited to only RVFV but also includes the unrelated RNA viruses EBOV (Class I fusion protein), ANDV (Class II fusion protein), and VSV (likely Class III fusion protein). The mechanism by which our peptides work entails the peptides binding to the virion and/or cell membrane, in a way that it will enter the cell with the virus so as to traffic with the virus into the endocytic pathway. Upon acidification and rearrangement of Gc, the peptide is able to bind to Gc and prevent successful fusion of the viral and endocytic membranes, thus inhibiting a successful viral infection.

The present invention is based on novel, broad-spectrum antiviral peptides, compositions containing one or more of these peptides, as well as the methods of using them to inhibit fusion of and productive infection by the RVFV, EBOV, ANDV, and/or VSV in a host. These peptides may be useful as prophylactic or therapeutic countermeasures against these viruses.

This invention is advantageous for several reasons. First, due to the small size of the peptides (about 20 amino acids), these would be easy to produce in large quantities, be stored for long periods of time and therefore could be a useful prophylactic or therapeutic in the event of exposure or infection with RVFV, EBOV, VSV, and/or ANDY. Also, these peptides (and preferably RVFV-6 and RVFV-10) may be used as an ideal tool for investigating the mechanism of viral entry and fusion processes of these viruses in vitro, as such resources are limited. Since these peptides bind to the surface of the host cells at the cell membrane and/or the virus membrane, traffic through the endocytic pathway, and are not toxic to the host cells, these peptides may be used as a drug delivery vehicle for drug s or therapeutics tethered or conjugated otherwise attached to them.

In a main embodiment, our invention is a broad-spectrum antiviral small peptide selected from the group of peptides consisting of RVFV-5, RVFV-7, RVFV-8, RVFV-9, and preferably, RVFV-6 or RVFV-10, that can be used individually or in any combination with each other, to inhibit fusion of RVFV, EBOV, VSV, and/or ANDY, or potentially other bunyaviruses or filoviruses (e.g., Hantaan virus, Puumala virus, Sin Nombre virus, and Dobrava virus). In particular, this embodiment covers the isolated antiviral RVFV peptides having the amino acid sequence selected from the group consisting of WNFFDWFSGLMSWFGGPLKLY (SEQ ID NO:5), designated RVFV-5,
WNFFDWFSGLMSWFGGPLK (SEQ ID NO:6), designated RVFV-6,
WNFFDWFSGLMSWFGGPLKTI (SEQ ID NO:7), designated RVFV-7,
SWNFFDWFSGLMSWFGGPLK (SEQ ID NO:8), designated RVFV-8,
SGSWNFFDWFSGLMSWFGG (SEQ ID NO:9), designated RVFV-9,
and SGSWNFFDWFSGLMSWFGGPL (SEQ ID NO:10) designated RVFV-10.

The peptide of RVFV-10 (SEQ ID NO:10) is preferred, and RVFV-6 (SEQ ID NO:6) is most preferred. We demonstrated a mechanism of action for RVFV-6, which we view as representative of the other peptides of our invention. This mechanism of action indicates that our peptides can inhibit productive infection of many viruses, and therefore it is within the scope of the present invention that our peptides have broad applicability in therapeutic intervention against other viruses in addition to those that were tested herein.

The invention further relates to compositions containing one or more of these peptides, and the use of these peptides in treating, preventing, and/or inhibiting HFVs or VSV. For instance, our peptides can be used in a prophylactic or therapeutic composition to protect the military and the civilian population from exposures against these viruses.

When stored or in preparation for use, these antiviral RVFV peptides are preferably suspended in solution of DMSO and water. Other solvents besides DMSO are possible, as long as the solvent is a biologically compatible medium. A substitute for water may be phosphate buffered saline. Preferably, the solution is a pharmaceutically acceptable carrier.

Antiviral peptides within the scope of the present invention include RVFV-5 through RVFV-10 (see Table 1). Of these peptides, we found RVFV-6 and RVFV-10 of particular interest. RVFV-6 especially was able to strongly inhibit the HFVs RVFV, EBOV, and ANDV as well as the agricultural virus VSV; and RVFV-10 was able to strongly inhibit RVFV and EBOV. However, all of RVFV-5-RVFV-10 are able to significantly inhibit RVFV, EBOV and VSV.

In another embodiment, our invention covers a method of inhibiting the fusion of RVFV, EBOV, and/or VSV to a target cell (in vivo or in vitro), comprising the steps of a) exposing one or more of the above-described peptides RVFV-5-RVFV-10 to a virion of RVFV, EBOV or VSV under conditions that the peptide attaches to or binds to or associates with the virion (e.g., forming a virion-peptide complex), and b) allowing the virion bound or attached or associated with the peptide (virion-peptide complex) to enter the target cell by natural entry processes and bind to a fusion protein, so that the fusion protein does not fuse the viral and cellular membranes together. (As used herein, when the peptide is described as binding to the virion or cell membrane in step a), the term "binds" is intended to cover any way that the peptide attaches or associates with either the viral membrane or cell membrane.) After the virion-peptide complex enters the target cell, natural acidification occurs in order so as to permit the optimal conditions for the peptide to bind to the fusion protein. One of the novel aspects of our invention is that it utilizes natural processes of the virion and the cell. Once a peptide is exposed to the virus, it binds or attaches or associates with either the viral membrane or the cell membrane, or to both. It if binds, etc. to the virus, it will enter into the cell with the virus by natural processes, carrying the peptide, through the endocytic pathway. If the peptide binds, etc. to the cell membrane (e.g., coats it), when the virus enters through the cell membrane the peptide will attach or bind or associate with the virus and traffic with the virus into the cell. In other words, the peptide associates with the viral and/or cellular membrane such that the peptide forms a complex with the virion as the virion enters into the cell (now carrying the peptide) via the endocytic pathway.

During endosomal acidification, the cell causes the pH to decrease within the endosome. In response to the lowered pH, the fusion protein rearranges to expose the peptide binding site. The novel antiviral peptide then binds fusion protein, which physically prevents the completion of the fusion protein rearrangement and fusion of the cell and virion membrane. In this way, fusion is inhibited, and true productive infection by the virion is prevented.

The preferred peptides are RVFV-10 and RVFV-6 (most preferred). If this method is carried out in vivo, any mode of administration as described here or that is otherwise well known is acceptable.

Another embodiment covers a method for preventing, treating or inhibiting post-exposure infection in a mammal by RVFV or VSV, or EBOV, comprising the step of administering to a mammal that has been exposed or potentially will be exposed to RVFV, VSV and/or EBOV an antiviral composition comprising one or more of the RVFV peptides RVFV-5-RVFV-10 described herein. The peptide(s) can be suspended in water with a pharmaceutically acceptable carrier (or biologically compatible medium). For instance, the peptide may be suspended in a solvent (such as DMSO) and water. The mammal can be a human, or domestic animal. The composition may be administered by any known means, for instance, intravenously (preferred), intramuscularly, parenterally, or subcutaneously.

In this method, if the mammal has already been exposed to RVFV, VSV or EBOV, the composition could be administered therapeutically in a dosage appropriate to the species and size of the subject, as would be understood by someone skilled in this art. As an example, dosing may be by injection at least twice a day.

If the mammal is not believed to have been exposed to RVFV, VSV or EBOV, but may soon be exposed to any of these viruses, the composition is administered prophylactically (preferably within 12-24 hours of exposure) in a dosage appropriate to the species and size of the subject, as would be understood by someone skilled in this art. As an example, dosing may be by injection at least twice a day.

Another embodiment covers an antiviral composition for treating, preventing or inhibiting infection in a mammal by RVFV or VSV, or EBOV, comprising one or more of the RVFV peptides RVFV-5-RVFV-10 described herein (and preferably RVFV-10, most preferably RVFV-6), suspended in water or phosphate buffered saline with a pharmaceutically acceptable carrier.

Another embodiment covers an antiviral composition for treating, preventing or inhibiting infection in a mammal by ANDV, comprising RVFV-6, suspended in water or phosphate buffered saline and/or with a pharmaceutically acceptable carrier.

Related to this, another embodiment covers a method of inhibiting the fusion of ANDV to a target cell, comprising the steps of a) exposing the RVFV-6 peptide to a virion of ANDV under conditions that the peptide binds to the virion (e.g., forming a virion-peptide complex), and b) allowing the virion bound with the RVFV-6 peptide (virion-peptide complex) to enter the target cell by natural entry processes and bind to a viral fusion protein, so that the fusion protein does not fuse the viral and cellular membranes together. After the virion-peptide complex enters the target cell, natural acidification occurs in order so as to permit the optimal conditions for the peptide to bind to the fusion protein. As described above, our methods using the peptides avail the natural processes of the virion and the cell. Thus, fusion is uniquely inhibited, and true productive infection by the virion is prevented. The peptide may be suspended in water with a pharmaceutically acceptable carrier or biologically compatible medium.

In another embodiment, this invention covers a method for preventing, treating or inhibiting post-exposure infection in a mammal by Andes Virus, comprising the step of administering to a mammal that has been exposed or potentially will be exposed to ANDV (preferably within 12-24 hours prior to exposure) an antiviral composition comprising the RVFV-6 peptide, suspended in water with a pharmaceutically acceptable carrier. For instance, the peptide may be suspended in a solvent and water (such as DMSO in either water or phosphate buffered saline). The mammal can be a human or domestic animal. The composition may be administered by any known means, for instance, intravenously (preferred), intramuscularly, parenterally, subcutaneously.

If the mammal has already been exposed to ANDV, the composition is administered in a dosage that is appropriate to the species and size of the subject, as would be understood by someone skilled in this art. As an example, dosing may be at least by injection twice a day.

If the mammal is not believed to have been exposed to ANDV, but may soon be exposed to it, the composition is administered preferably within 12-24 hours of exposure, in a dosage that is appropriate to the species and size of the subject, as would be understood by someone skilled in this art. As an example, dosing may be at least by injection twice a day.

In another embodiment, our invention covers a composition comprising at least one of the RVFV peptide described herein (RVFV-5-RVFV-10), which is tethered or conjugated to a drug or therapeutic, so as to form a peptide-drug or peptide-therapeutic composition or complex. Since the broad-spectrum antiviral peptides herein are very small, bind to the surface of host cells, traffic through the endocytic pathway, and are not toxic to host cells, these peptides may be used as a drug delivery vehicle to tether unrelated drugs to the plasma membrane or endocytic compartment of a cell. The drug or therapeutic having a site of action described herein is selected from the group consisting of a component capable of being conjugated to a peptides or a peptide modified to allow drug conjugation. These techniques for conjugation are known in the art.

In a related embodiment, the invention covers a method of delivering a drug or therapeutic to a target cell in a subject, comprising the step of administering to the subject the peptide-drug composition/complex or peptide-therapeutic composition/complex described here, under conditions that the drug or therapeutic is delivered to a target cell in the subject. The drug or therapeutic is tethered or conjugated to the peptide by methods known in the art, so as to form a peptide-drug complex or a peptide-therapeutic complex. The drug would be attached to the peptide by known means (e.g., by direct link to an amino acid, or via a compound to the peptides by which the drug could then be attached).

In another embodiment, our novel peptides can be useful for prophylactic and therapeutic uses during such epidemics or for potential laboratory exposure with one of these viruses.

These peptides could be of additional biomedical use to study mechanisms of viral fusion or by utilizing its likely membrane-binding properties. The present invention provides a method for investigating the mechanism of viral entry and fusion processes of RVFV, EBOV, ANDV and VSV in vitro using one or more of the broad-spectrum antiviral peptides herein.

As used herein, the term "patient" or "subject" refers to an organism to which viruses of the invention can be administered. Preferably, a patient is a bird or a mammal, e.g., a human, primate, livestock animal, or a rodent For all of the compositions and methods of this invention, they may, as appropriate, be administered to the patient in a biologically compatible solution or a pharmaceutically acceptable delivery vehicle, by administration either directly into cells or systemically (e.g., intravenously), subcutaneously, parenterally, intramuscularly, and the like. Suitable pharmaceutical formulations, in part, depend upon the use or the route of entry, for example transdermal, or by injection. Such forms should not prevent the composition or formulation from reaching a target cell (i.e., a cell to which the virus is desired to be delivered to) or exerting its effect. For example, pharmacological compositions injected into the blood stream should be soluble.

While dosages administered will vary from patient to patient (e.g., depending upon the size of the patient), a "therapeutically effective dose" will be determined by setting as a lower limit, the concentration of peptide proven to be safe and escalating to higher doses, while monitoring for any deleterious side effects. Escalating dose studies are routine in the art (see, e.g., Nies and Spielberg, "Principles of Therapeutics," In Goodman & Gilman's The Pharmacological Basis of Therapeutics, eds. Hardman, et al., McGraw-Hill, NY, 1996, pp 43 62).

The above-identified statements are provided to briefly describe the present invention. They are provided for example purposes only, and are not intended to limit the scope of the present invention.

BRIEF DESCRIPTION OF THE DRAWINGS

FIG. 4 shows a graphical representation of the toxicity of the second iteration of peptides, RVFV-6 through RVFV-10, using Vero E6 cells using an MTT assay. Cells were incubated for approximately 18 hours with peptide, and cellular proliferation (a surrogate for cell viability) was measured using an enzymatic substrate in a colorimetric assay.

FIG. 5 (A-D) shows a graphical representation of RVFV-6 and RVFV-10 inhibition of RVFV (Figure A), EBOV (Figure B), and ANDV (Figure C) as well as a more detailed toxicity analysis of RVFV-6 showing it is non-toxic to cells (Figure D). Serial dilutions of peptide was incubated with RVFV-Zh501 (Figure A), EBOV-eGFP (Figure B), or ANDV (Figure C) before infecting a monolayer of Vero E6 cells. Plaques were counted for RVFV and ANDV, and the reduction in the number of plaques was determined using the number of plaques from the virus-only control. For EBOV, the GFP signal (as a surrogate for viral replication) was measured post-infection, and the percent inhibition was determined using the virus-only input control. Peptide toxicity was measured by a MTT assay (Figure D), as described in FIG. 2 (A and B) and FIG. 4, for serially diluted RVFV-6 and RVFV-6sc. These data were previously published by the inventors (Koehler, Smith et al. 2013).

FIG. 8 (A and B) shows RVFV-6 binds to the RVFV virion and not to Gc initially but does bind to Gc following the conformational changes induced by acidification. Activation of the viral fusion process is required for RVFV-6 binding to RVFV-Gc and VSV-G. (Figure A) Biotin-conjugated RVFV-6, scrambled RVFV-6, or no peptide was pre-bound to avidin beads prior to the addition of RVFV-MP12 (Figure A) or VSV-pseudotyped VSV-luciferase (Figure B). Peptide binding to VSV fusion protein. Beads were washed to remove unbound virus and treated as indicated with 1) lysis buffer and wash, 2) pH 5.2 treatment followed by lysis buffer and wash, or 3) no pH 5.2 treatment and no lysis buffer. Protein bound to the avidin beads were resolved by SDS-PAGE and probed with the anti-RVFV-Gc antibody 4D4. These data were previously published by the inventors (Koehler, Smith et al. 2013).

FIG. 9 (A and B) illustrates RVFV-6 prevents the fusion process initiated by acidification. RVFV-6 inhibits both RVFV and VSV cell:cell fusion. Vero E6 cells were transfected with mammalian expression plasmids expressing either the RVFV glycoproteins Gn and Gc or the VSV glycoprotein G. Twenty-four hours later, cells were harvested and seeded into 8-well chamber slides. Eighteen hours later, cells were incubated for one hour with 50 M RVFV-6 peptide followed by a pH 5.2 treatment for 15 minutes. cEMEM was added to raise the pH, and slides were incubated for 5 hours prior to methanol fixing and Giemsa staining. Fusion events are shown in (Figure A) with arrows indicating fusion events. Pictures were taken at 100x. (Figure B) Quantification of fusion inhibition. Fusion events were quantified by counting the number of events in 5 fields of view over two separate wells (10 total fields of view, at 200x). RVF-RVFV-6 and VSV-RVFV-6 are peptide-treated cells transfected with RVFV Gn/Gc and VSV-G, respectively, and RVF and VSV were treated with no peptide. Statistical significance was assessed by a paired, two-tailed t test. *($p=0.001$); **($p<0.0001$). These data were previously published by the inventors (Koehler, Smith et al. 2013).

DETAILED DESCRIPTION OF THE INVENTION

Figure 1C:
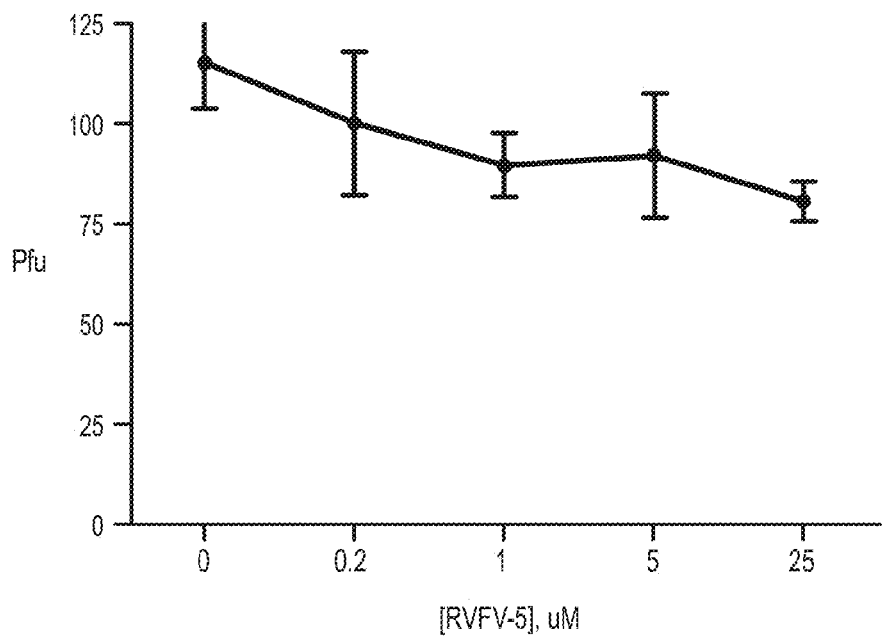
FIG. 1(A-D) provides a graphical representation of the inhibition of RVFV-MP12 by peptide RVFV-5. Serial dilutions of the peptide RVFV-5 or carrier were incubated with approximately 75 pfu (Figure A) or 100 pfu (Figure C) of MP12 for one hour and then was used to infect confluent Vero E6 cells. The number of plaques was counted (Figure A and Figure C). Percent inhibition was calculated based on the carrier pfu counts (Figure B and Figure D), where virus-only control is 100%.

A design approach was previously developed by inventor Dr. Robert Garry at Tulane University to predict regions of the viral fusion protein that might be inhibitory when introduced to the virus as an analogous peptide (19, 31). This approach has had some success with the identification of inhibitory peptides for SARS-coronavirus (31) and the flaviviruses West Nile virus and DENV (19). Although targeting the viral entry process with fusion inhibiting peptides has proven successful with multiple viruses such as the flavivirus dengue virus (8, 19, 32), SARS coronavirus (31), and HIV-1 (21, 39), the mechanism of action of various fusion inhibitors appear to differ, and there is no fool-proof design mechanism in place to predict what characteristics would constitute a functional peptide or protein inhibitor.

However, we did successfully design peptides to disrupt the normal fusion process of RVFV fusion protein Gc in order to prevent the virion from productively infecting targeted host cells. We found that several of these peptides inhibited RVFV infection in vitro. In further characterizing these peptides, we determined the peptides were not toxic, did not interfere with virion:cell binding, and disrupted the fusion process critical for a successful viral infection. In addition to inhibiting RVFV infection, we surprisingly found that the most promising of these inhibitors, RVFV-6 has broad activity in inhibiting the infectivity of several diverse viruses including ANDY, a hantavirus, utilizing a class II fusion protein (35), EBOV, a filovirus, utilizing class I fusion protein (24, 38), and VSV, a rhabdovirus likely using a class III fusion protein (29, 30). This peptide, as well as others within the scope of the present invention, could individually or in combination be utilized as a prophylactic or therapeutic for RVFV, EBOV, ANDY, or VSV exposure or infection, and these peptides have the potential for broad prophylactic and therapeutic applicability against other pathogenic viruses using Class I, Class II, or Class III fusion mechanisms.

Some issues to consider—and obstacles to overcome—to design peptide inhibitors of viral entry were (1) the enveloped viruses need to cross two membranes (viral and cellular) to deliver the viral core; (2) viral fusion proteins mediate fusion of the viral and cellular membranes; and (3) unsure to what extent peptides analogous to different fusion proteins can inhibit virus infectivity.

In an effort to identify peptides that inhibit RVFV infection, the RVFV Gc amino acid sequence (GenBank ID P03518) was analyzed to identify regions of the protein having a positive Wimley-White interfacial hydrophobicity score (WWIHS), indicating a potential to interact with lipid bilayers (34). To the best of their knowledge, the inventors were the first to identify these regions using this methodology. Five non-transmembrane domain regions within RVFV Gc were found to have significant WWIHS values.

Peptides analogous to these five regions were designed and synthesized—RVFV-1 through RVFV-5 (Table 1, RVFV-1 through RVFV-5). The amino acid sequence, position, and the protein domain location for these and for all peptides used herein are provided in Table 1.

TABLE 1

Description of the peptides designed and evaluated for inhibition of virus infectivity. Peptide amino acid sequences are analogous to the domain and location within RVFV Gc

| peptide | Sequence | domain | location |
| --- | --- | --- | --- |
| RVFV-1 | YWTGSISPKCLSSRRCHLV | IIa | 72-90 |
| RVFV-2 | WGCGCFNVNPSCLFVHTYL | IIa (fusion peptide) | 131-149 |
| RVFV-3 | LGASSSRFTNWGSVSLSLD | IIb | 185-203 |
| RVFV-4 | FVGAAVSCDAAFLNLTGCY | III | 332-350 |
| RVFV-5 | WNFFDWFSGLMSWFGGPLKLY | stem | 450-470 |
| RVFV-6 | WNFFDWFSGLMSWFGGPLK | stem | 450-468 |
| RVFV-7 | WNFFDWFSGLMSWFGGPLKTI | stem | 450-470 |
| RVFV-8 | SWNFFDWFSGLMSWFGGPLK | stem | 449-468 |

TABLE 1-continued

Description of the peptides designed and evaluated for inhibition of virus infectivity. Peptide amino acid sequences are analogous to the domain and location within RVFV Gc

| peptide | Sequence | domain | location |
| --- | --- | --- | --- |
| RVFV-9 | SGSWNFFDWFSGLMSWFGG | stem | 447-465 |
| RVFV-10 | SGSWNFFDWFSGLMSWFGGPL | stem | 447-467 |
| RVFV-6sc | MFLGWSFDFGSLWGNKPWF | stem | 450-468 |
| RVFV-10sc | WSSGLPFGNFGLSWFDMGFWS | stem | 447-467 |

The sequence corresponding to each peptide in Table 1 is identified and referenced herein as follows:
Sequence corresponding to RVFV-1=SEQ ID NO. 1
Sequence corresponding to RVFV-2=SEQ ID NO. 2
Sequence corresponding to RVFV-3=SEQ ID NO. 3
Sequence corresponding to RVFV-4=SEQ ID NO. 4
Sequence corresponding to RVFV-5=SEQ ID NO. 5
Sequence corresponding to RVFV-6=SEQ ID NO. 6
Sequence corresponding to RVFV-7=SEQ ID NO. 7
Sequence corresponding to RVFV-8=SEQ ID NO. 8
Sequence corresponding to RVFV-9=SEQ ID NO. 9
Sequence corresponding to RVFV-10=SEQ ID NO. 10
Sequence corresponding to RVFV-6sc=SEQ ID NO. 11
Sequence corresponding to RVFV-10sc=SEQ ID NO. 12

Figure 2A:
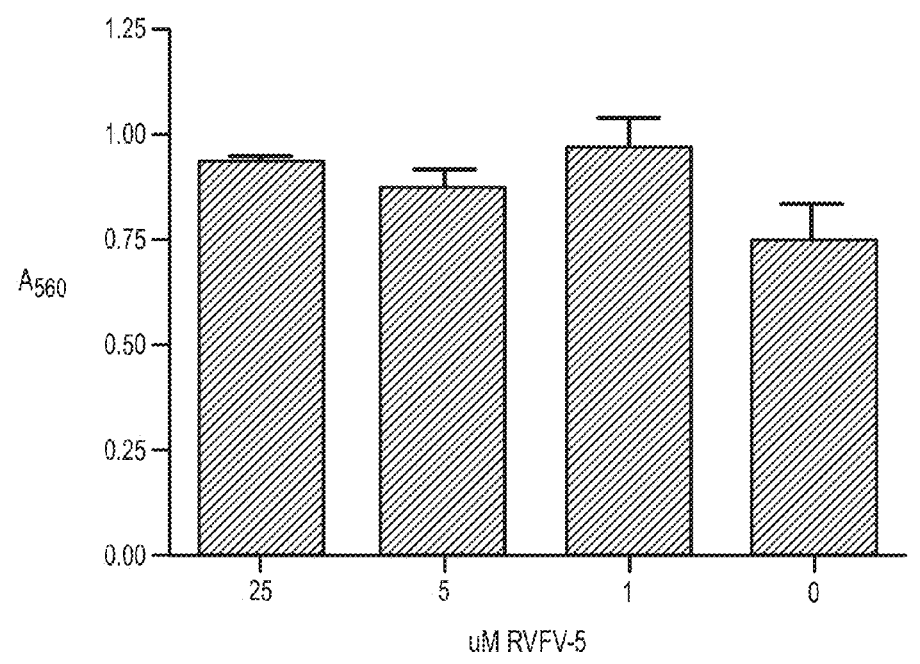
Figure 2B:
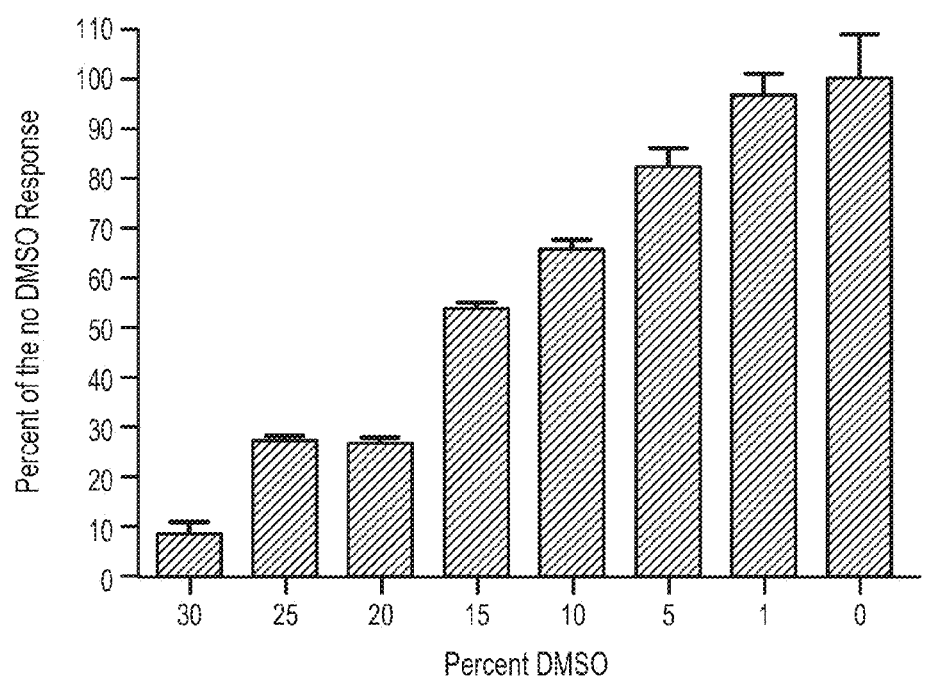
FIG. 2 (A and B) provides a graphical representation of toxicity data of RVFV-5 peptide and DMSO, a component of the peptide carrier, using a cell proliferation assay. The toxicity of RVFV-5 (Figure A) and DMSO, used in the peptide resuspension buffer, (Figure B) was determined using a MTT cell proliferation assay. Vero E6 cells were incubated for 24 hours with dilutions of peptide or no peptide (Figure A) or medium with decreasing percent DMSO (Figure B). Cellular proliferation is measured using an enzymatic substrate in a colorimetric assay. The impact of DMSO is presented as a percentage of the no DMSO proliferation response.

Synthetic peptides RVFV-1 (SEQ ID NO. 1), RVFV-2 (SEQ ID NO. 2), RVFV-3 (SEQ ID NO. 3), RVFV-4 (SEQ ID NO. 4), and RVFV-5 (SEQ ID NO. 5), also referred to herein as synthetic peptides RVFV-1 through RVFV-5, or SEQ ID NO. 1 through SEQ ID NO. 5, were evaluated for inhibition of RVFV-MP12, a vaccine strain of RVFV (6), using a plaque reduction assay described herein. Only RVFV-5 demonstrated any inhibition—approximately 30% inhibition (data for RVFV-5 shown in FIG. 1). Toxicity data for RVFV-5 and DMSO (the peptide carrier) show these components are not toxic to cells at the concentrations used here (FIG. 2).

Figure 3A:
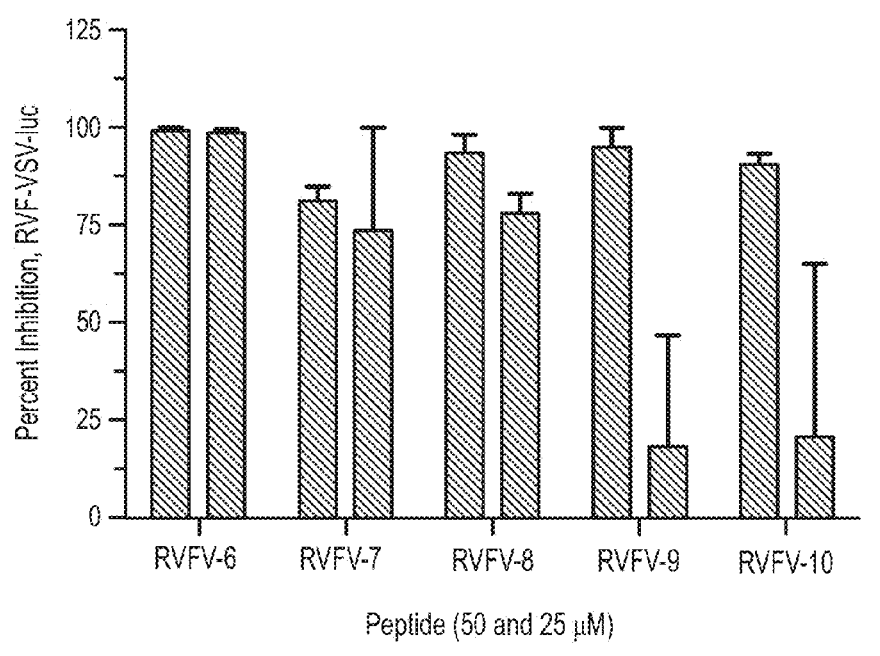
Figure 3B:
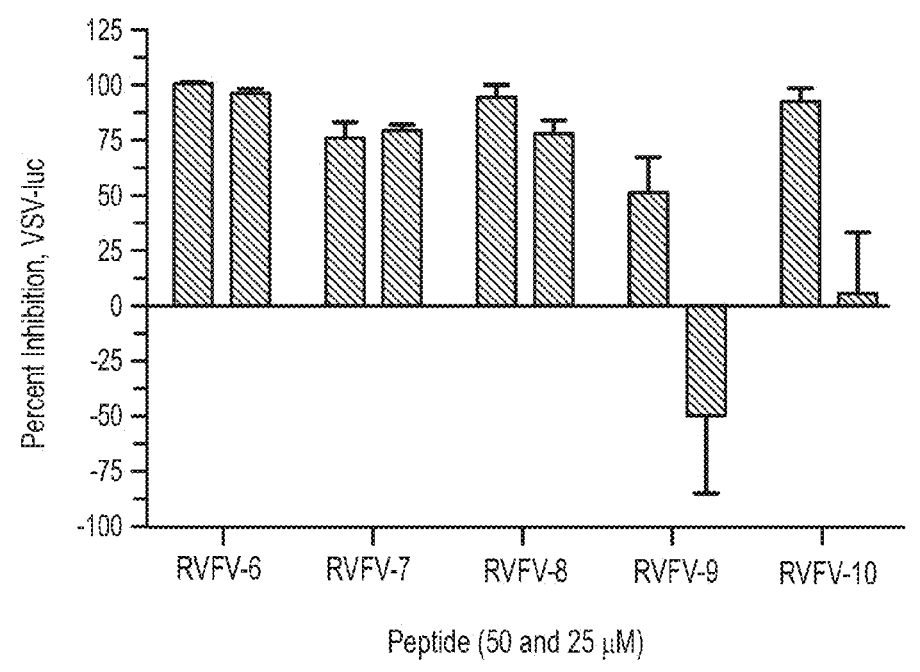
Figure 3C:
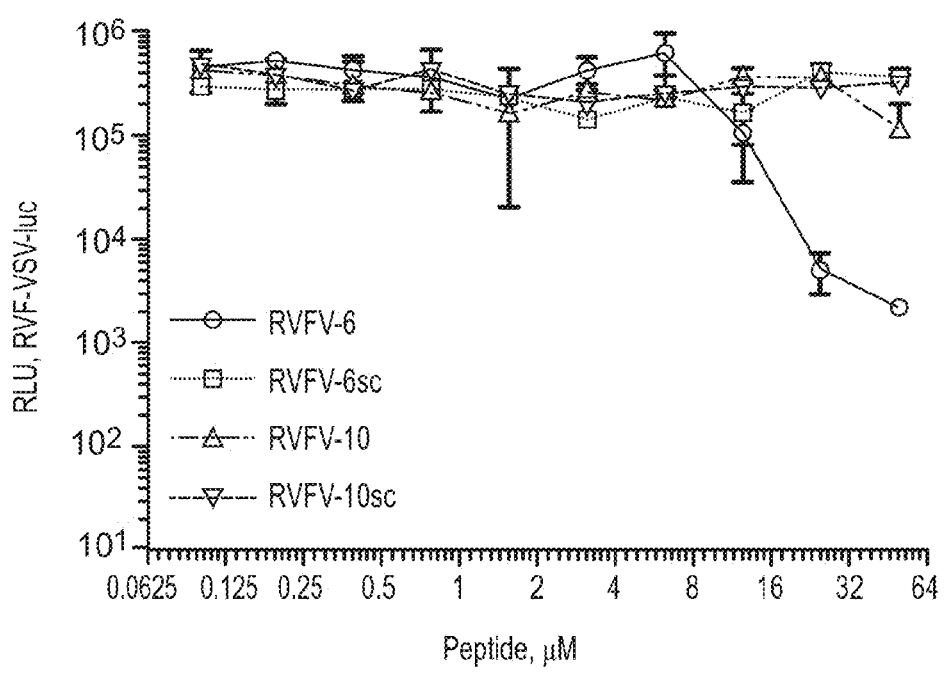
Figure 3D:
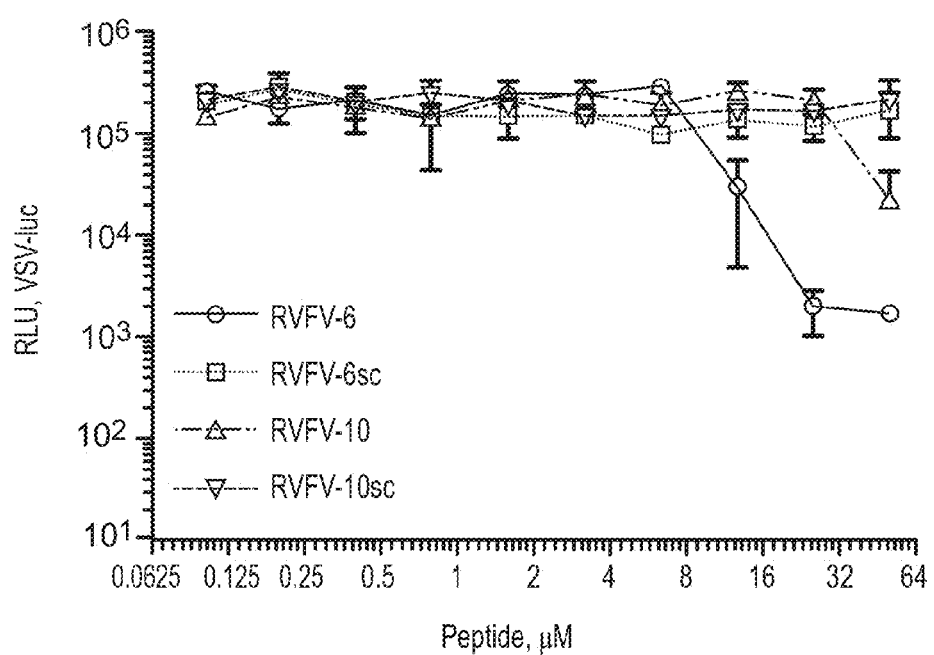
FIG. 3 (A-D) provides a graphical representation of inhibition of both RVF and VSV pseudotyped virus by the second iteration of RVFV peptides based on RVFV-5. Peptide at 50 or 25 mM concentrations was incubated with either a RVF-VSV-luc (Figure A) or VSV-luc reporter virus (Figure B) for one hour prior to infecting a monolayer of Vero E6 cells. Luciferase activity (as a surrogate for viral replication) was measured approximately 18 hours later. Percent inhibition was calculated using the luciferase signal of the virus-only input control. Serial dilutions of peptide [RVFV-6, RVFV-10, or scrambled versions of RVFV-6 (RVFV-6sc) or RVFV-10 (RVFV-10sc)] were incubated with either a RVF-VSV-luc (Figure C) or VSV-luc reporter virus (Figure D) for one hour prior to infecting a monolayer of Vero E6 cells. Luciferase activity (as a surrogate for viral replication) was measured approximately 18 hours later. These data were previously published by the inventors (Koehler, Smith et al. 2013).
Figure 4:
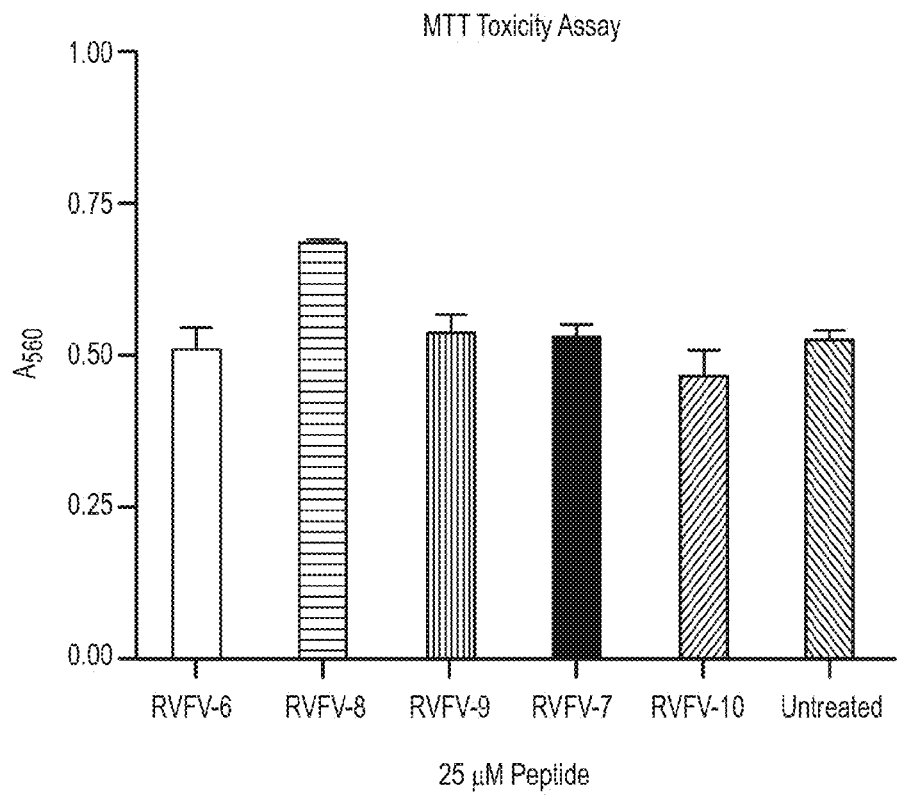

From RVFV-5, five additional peptides were developed, and all of these have nontoxic antiviral properties (FIGS. 3-5). The antiviral peptides within the scope of the present invention include those specifically identified herein as SEQ ID NO. 5, SEQ ID NO. 6, SEQ ID NO. 7, SEQ ID NO. 8, SEQ ID NO. 9 and SEQ ID NO 10. All of these include at least some of the Gc stem region.

As described here, our novel peptides, individually or in combination, may be suitable for use in treating, preventing and/or inhibiting infection by hemorrhagic fever viruses—primarily RVFV, EBOV, and ANDV, as well as the agricultural virus VSV.

Among the peptides designed, we found RVFV-6 and RVFV-10 to be the best antivirals and inhibitors of virus fusion and infectivity, and these two are therefore the preferred peptides (RVFV-6 being the most preferred).

We discovered that our RVFV peptides exhibited broad antiviral activity and inhibition of multiple viruses including EBOV (Class I fusion protein), RVFV and ANDV (Class II fusion proteins), and VSV (likely a Class III fusion protein). Specifically, RVFV-5, RVFV-7, RVFV-8, RVFV-9, and RVFV-10 are believed to be effective inhibitors of the fusion (and therefore infection) of RVFV, VSV and EBOV. RVFV-6 is also an effective inhibitor of these, and also ANDV. Importantly, these peptides are not toxic to the host cells.

Although the invention is described at points herein with reference to RVFV-6 and RVFV-10, we view these as representative of all the antiviral peptides. Our invention is not intended to be limited to only RVFV-6 and RVFV-10, as would be understood by someone skilled in this art from a fair reading of our whole description.

Our antiviral synthetic RVFV peptides, and their corresponding methods of use, have at least the following novel properties: (1) the ability to inhibit RVFV and VSV fusion and infectivity, and (2) the ability to inhibit EBOV and ANDV infectivity using one or more of the antiviral synthetic RVFV peptides. By the term "fusion", it is meant the merger of the viral and cellular membranes such that the viral genome enters the cell. The term "infection" in reference to a subject is viral exposure and active viral replication. The term "infection" in reference to a cell is the successful entry of the virus into the cell—a productive infection occurs where the virus successfully replicates and generates new virus; whereas if no successful replication of the virus occurs, this would be a nonproductive infection (e.g., brought about when one of the novel antiviral peptides inhibits fusion between viral and cellular membrane). In other words, with our methods using the antiviral peptides, the virus enters the cell as a virion-peptide complex—and technically infects the cell—but the antiviral peptide prevents productive infection.

The peptides may be synthesized using well known and commercially available methodologies and/or services provided within the industry for such purposes—i.e., the labs at Bio-synthesis, Inc. (Lewisville, Tex.), etc.

As described above, one embodiment is the antiviral peptides themselves. For practical purposes of storage and use, the peptides can be suspended in a biologically compatible medium or a pharmaceutically acceptable carrier. An example is a solution of DMSO and water, which is very useful for most of the purposes contemplated for our peptides.

In one of its basic methods of use, one or more of our peptides can be used in a method of inhibiting fusion and productive infectivity of RVFV, VSV, EBOV and/or ANDV to a target cell in a host (e.g., a host cell in mammal, or in vitro). For RVFV, VSV and EBOV, the steps include exposing one or more of the above-described peptides RVFV-5-RVFV-10 (RVFV-6 being most preferred) to a virion of RVFV, VSV, or EBOV under conditions that the peptide binds or attaches to or associates with the virion membrane and/or the cell membrane, forming a complex between the virion and the peptide. The peptide-virion complex is allowed to enter the target cell via the natural viral entry process. As described above, the cells natural acidification process lowers the pH at the binding area, so that the viral fusion protein rearranges, exposing the binding site of the peptide. The peptide then binds to a fusion protein produced by the virion so that the fusion protein physically cannot complete its low-pH triggered rearrangements that drive the fusion of the endocytic membrane and the viral membrane. Thus, fusion of the virion is interrupted, and productive infection is inhibited. The peptide prevents the viral genome from entering into the cell by preventing the fusion protein from completely rearranging to bring both membranes into close proximity to destabilize and merge.

For ANDV, the method to inhibit fusion and productive infection is similar, but the preferred peptide to use is RVFV-6.

The peptides can be combined with other ingredients—in fact, any ingredients that are appropriate and do not destroy or modify the peptides in any significant way—to form compositions. For instance, our invention covers antiviral compositions comprising one or more of the peptides, and a pharmaceutically acceptable carrier or the like. The antiviral composition may be used for treating, preventing or inhibiting infection in a mammal (e.g., human, livestock) of any of RVFV, VSV or EBOV, after the mammal has been exposed to one of these viruses (or is believed to have been exposed).

Another antiviral composition is useful against ANDV, and will comprise RVFV-6, and a pharmaceutically acceptable carrier or the like. The antiviral composition may be used for treating, preventing or inhibiting ANDV infection in a mammal (e.g., human, livestock) after the mammal has been exposed to ANDV (or is believed to have been exposed, or soon will be exposed).

Another method of our invention is for preventing, or treating or inhibiting post-exposure infection in a mammal by of any of RVFV, VSV or EBOV. An antiviral composition such as one described here is administered to a mammal (e.g., human, livestock) after the mammal has been exposed, or is suspected of having been exposed, or soon will be exposed, to RVFV, VSV or EBOV. A similar method of our invention is for preventing, or treating or inhibiting post-exposure infection in a mammal by of ANDY. An antiviral composition containing RVFV-6 as one described herein is administered to a mammal (e.g., human, livestock) after the mammal has been exposed, or is suspected of having been exposed, or soon will be exposed (e.g., within 12-24 hours), to ANDY. For these embodiments, and all the embodiments of our invention to which this is pertinent, the peptides may be administered to a subject using conventional routes of administration, such as injection (i.e., intravenous (i.v.), intramuscular (i.m.), and subcutaneous (s.c.)) or transdermal application. In addition, the peptides may be administered using well known pharmaceutically acceptable carriers. Selection of the route of administration and pharmaceutically acceptable carriers to employ in the administration of the present invention is well within the skill of the art. A person having ordinary skill in the art with knowledge of the invention as described herein would be able to determine suitable dosages to use for evaluation of and for use of the invention herein for the purposes described.

All of the antiviral compositions can be useful prophylactic and/or therapeutic agents in the event of exposure to or infection with RVFV, EBOV, ANDY, or VSV. The invention represents a broad-spectrum antiviral that could be used during a potential or confirmed exposure to one of these agents to protect the warfighter and the civilian population from exposure.

The following is a description of the development and testing of our novel peptides. Uses and variations of uses of our peptides will be apparent to someone skilled in this art.

The initial five RVFV synthetic peptides designed as described above (RVFV-1 through RVFV-5) were evaluated for inhibition of RVFV-MP12 using a plaque-reduction assay. Only RVFV-5 demonstrated inhibition (approximately 30%, FIG. 1). An MTT assay was conducted with RVFV-5 in order to assess peptide and peptide carrier toxicity to cells as this could be the mechanism for viral inhibition. The MTT assay is a common colorometric method that can be used to measure the cell viability. As tetrazolium salts are reduced only by metabolically active cells, only viable cells treated with 3-(4,5-dimethylthiazol-2-yl)-2,5-diphenyltetrazolium bromide (MTT) are able to reduce the compound to a blue colored formazan. This is an assay commonly used to measure peptide toxicity (Hrobowski, Garry et al. 2005; Sainz, Mossel et al. 2006;

Costin, Jenwitheesuk et al. 2010). Neither RVFV-5 nor the peptide carrier were toxic to cells at the concentrations used (FIG. 2).

In order to improve inhibition, additional peptides based on RVFV-5 were designed and synthesized, by adding or subtracting amino acids from the N- and C-termini of the RVFV-5 peptide. These additional peptides are identified in Table 1 as RVFV-6, RVFV-7, RVFV-8, RVFV-9, and RVFV-10 (also referred to herein as RVFV-6 through RVFV-10, or SEQ ID NO. 6 through SEQ ID NO. 10). These new peptides were assayed for inhibition using a pseudotyped reporter assay, either a RVFV-pseudotyped VSV-luc virus (the VSV core is tagged with the reporter gene luciferase, and the envelope is composed of the RVFV glycoproteins Gn and Gc) or a VSV-luc control virus. Each virus was incubated with either 50 or 25 μM peptide before infecting a monolayer of Vero E6 cells, and luciferase activity was measured as a surrogate for viral replication. Interestingly, all of the peptides inhibited both RVF-VSV-luc and the VSV-luc viruses (FIGS. 3 A and B). Inhibition of VSV-luc was unexpected since the VSV-G protein is likely a class III fusion protein. (Roche, Bressanelli et al. 2006; Roche, Rey et al. 2007).

Scrambled peptides for RVFV-6 and RVFV-10 were synthesized and designated RVFV-6sc and RVFV10sc. These peptides contain all of the amino acids found in RVFV-6 and RVFV-10, and the amino acid order was determined by random. Dose-response curved were generated for each of these peptides using the RVFV-VSV-luc (FIG. 3C) and VSV-luc (FIG. 3D) pseudoviruses. This showed RVFV-6 was the more potent inhibitor of these viruses while RVFV-6sc had minimal impact on viral infectivity. RVFV-6 through RVFV-10 were assessed using the MTT assay described above, and no cellular toxicity was observed (FIG. 4).

Figure 5A:
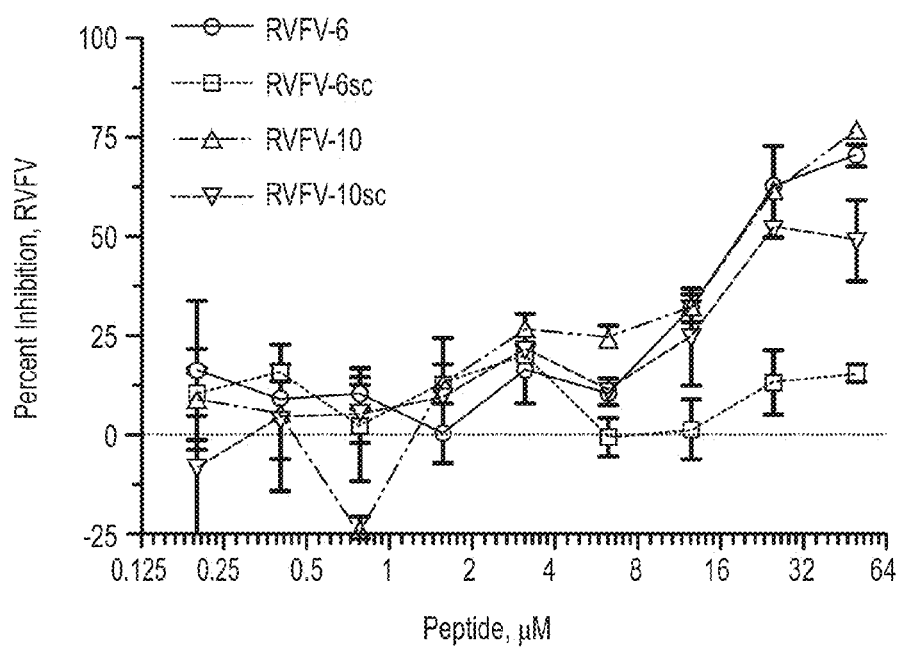
Figure 5B:
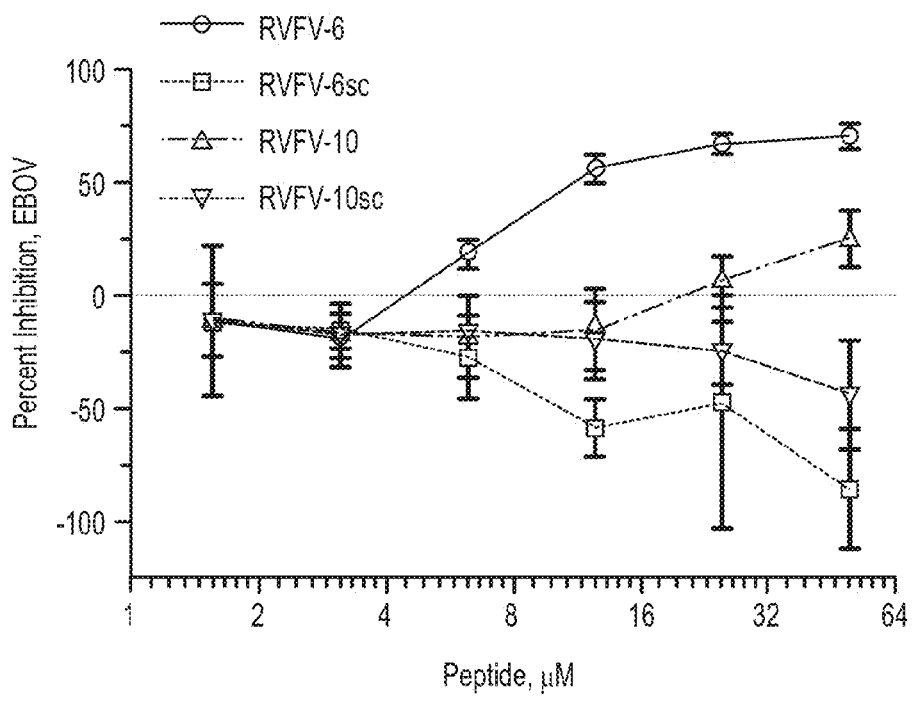
Figure 5C:
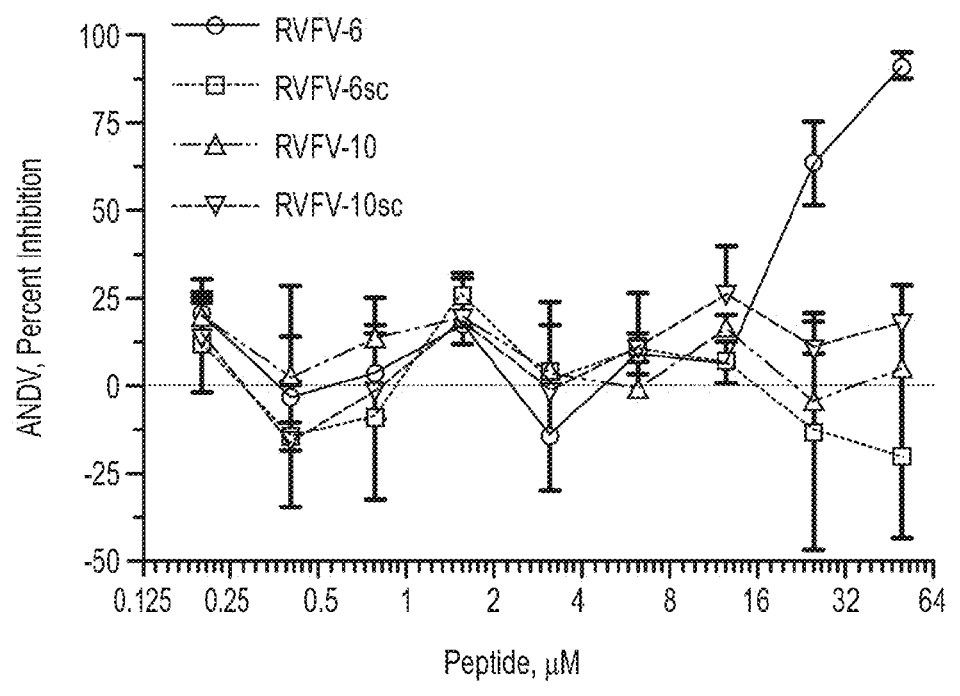
Figure 5D:
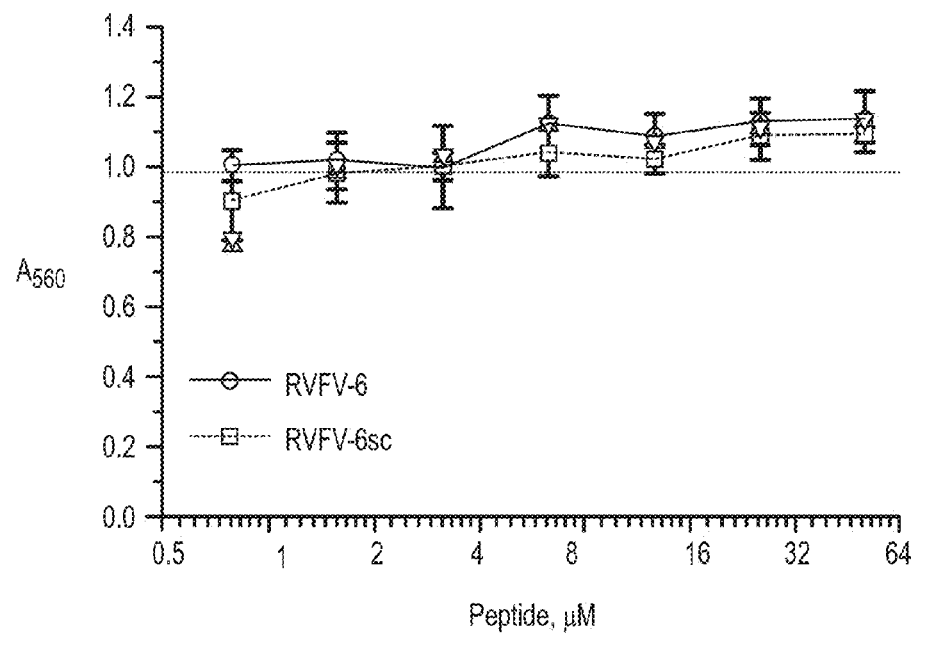

To confirm the pseudotyped virus findings, RVFV-6, RVFV-10, RVFV-6sc, and RVFV-10sc were tested for inhibition of the pathogenic RVFV strain Ah501 (FIG. 5A), showing potent inhibition of RVFV by both RVFV6 and RVFV10. These peptides were further tested for inhibition against EBOV (FIG. 5B) and ANDV (FIG. 5C) with RVFV-6 showing strong inhibition of both EBOV and ANDV. Since RVFV-6 performed the best against all of the tested viruses, RVFV-6 was selected for further evaluation. Toxicity of both RVFV-6 and RVFV-6sc was assessed in greater detail. An MTT assay was conducted as described above using 1:2 serial dilutions of peptide, showing there is little negative impact on cell proliferation (FIG. 5D).

The inventors next sought to identify the mechanism of action for the broad viral inhibition observed with RVFV, VSV, ANDV, and EBOV. Because RVFV-6 potently inhibited diverse viruses with varying fusion mechanisms, we sought to determine if RVFV-6 was preventing the virus from binding to the permissive cell as has been previously reported for DENV (Costin, Jenwitheesuk et al. 2010).

Figure 6A:
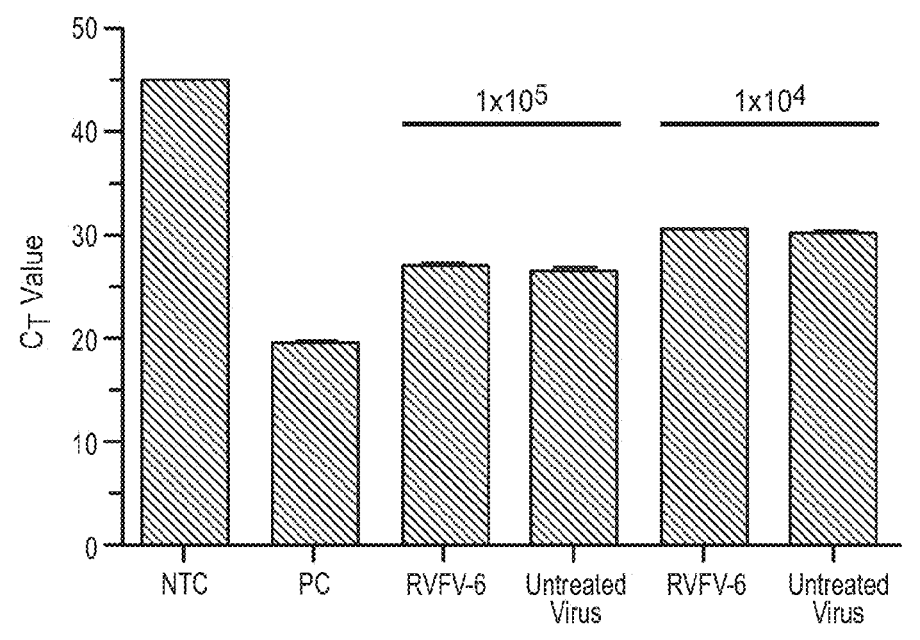
Figure 6B:
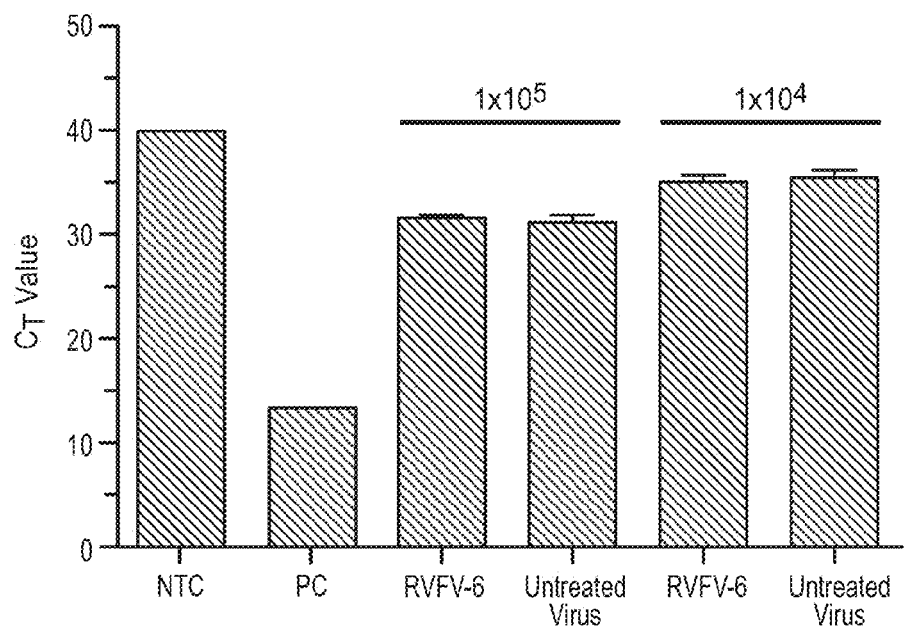
FIG. 6 (A and B) is a graphical representation showing RVFV-6 does not prevent virion binding to permissive cells. A real-time PCR assay was developed to assay if the peptide interferes with virion-cell binding. Two dilutions of RVFV-MP12 (Figure A) or EBOV (Figure B) were incubated with 50 uM peptide or untreated virus for one hour prior to infecting a monolayer of Vero E6 cells. Following the one hour infection, the cells were washed repeatedly with PBS, and RNA was harvested. Presence of viral RNA was determined by real-time PCR using established assays. $C_T$ values represent the PCR cycle at which the probe signal is positive. NTC is the no template control, positive is RNA purified from either RVFV-MP12 or EboZ-eGFP, and virus is the input virus incubated without peptide. These data were previously published by the inventors (Koehler, Smith et al. 2013).

To evaluate this, RVFV-MP12 (FIG. 6A) or EBOV (FIG. 6B) was incubated with or without RVFV-6 peptide prior to addition to Vero E6 cells. Cells were extensively washed with PBS to remove unbound virus, and a real-time PCR assay for RVFV (Drosten, Gottig et al. 2002) or EBOV (Trombley, Wachter et al. 2010) was used to measure the relative amounts of virus bound to permissive cells. If RVFV-6 prevented the virus from binding to permissive cells, this would be reflected in a decrease in the amount of viral RNA measured. For both RVFV and EBOV, this was not the case, indicating that the peptide was not inhibitory because it prevented binding to the target cell (FIG. 6).

Figure 7A:
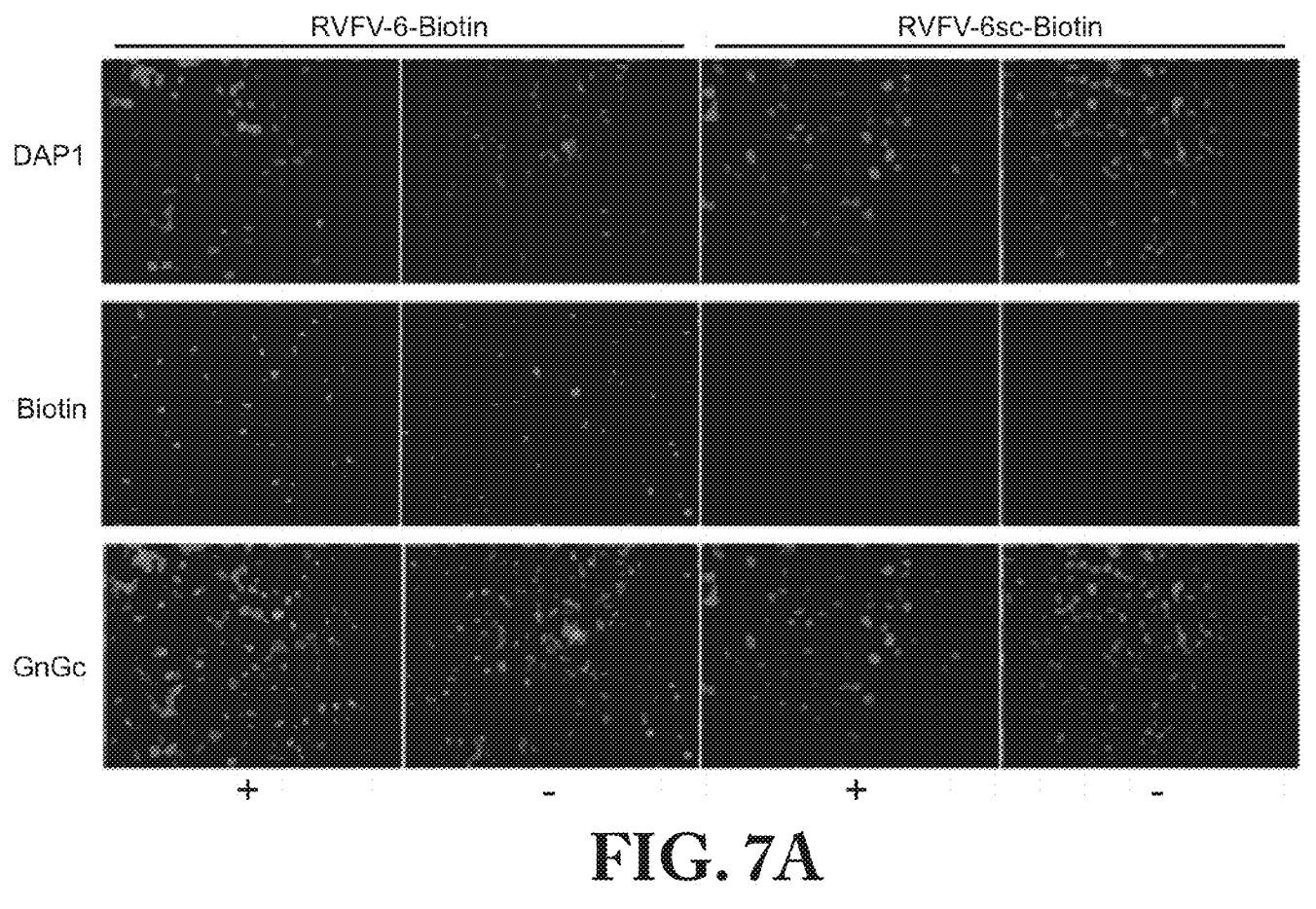

Since RVFV-6 did not interfere with the virus binding to permissive cells, viral inhibition must have been at a later stage of viral entry. As we anticipated RVFV-6 would bind to and interfere with RVFV fusion, we next wanted to know if peptide bound to the fusion protein Gc. To evaluate this, Vero E6 cells were transfected with a plasmid to express RVFV-GnGc and were incubated with either biotin-conjugated RVFV-6 or biotin-conjugated RVFV-6sc for 60 minutes. After washing with PBS and staining with an anti-biotin antibody, we found that RVFV-6 bound to Vero E6 cells independent of GnGc expression while RVFV-6sc did not bind to either cell type (FIG. 7). This binding was rapid and occurred even after a 30 second incubation with peptide (data not shown). These results with RVFV-6 are similar to those reported earlier for a fusion inhibitor peptide to DENV (Schmidt, Yang et al. 2010), in which the peptide was found to bind to the plasma membrane. Thus, we showed that the peptide binds to cells, that binding is independent of the glycoproteins being present, and the scrambled peptide does not bind to the cell so cell binding is peptide sequence dependent.

Figure 7B:
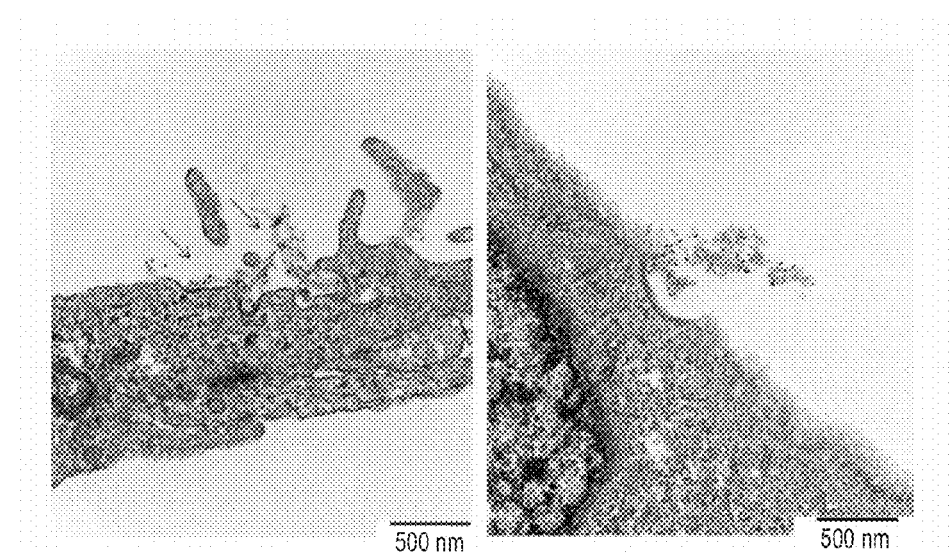
FIG. 7 (A and B) illustrates RVFV-6 binding to Vero E6 cells independent of RVFV-GnGc expression. (Figure A) Vero E6 cells were transfected with a plasmid expressing RVFV-GnGc. Forty-eight hours later, either the biotin-labeled RVFV-6 peptide or the biotin-labeled RVFV-6sc peptide was added to the cells for one hour prior to washing with PBS. Cells were fixed with 10% buffered formalin, and peptide binding was identified using an anti-biotin antibody conjugated to Texas Red. Nuclei were stained with DAPI (blue). (Figure B) Vero E6 cells were incubated with biotin-conjugated RVFV-6 and stained with a gold-conjugated anti-biotin antibody. Transmission electron microscopy was conducted to visualize peptide location on the cell surface (arrows). These data were previously published by the inventors (Koehler, Smith et al. 2013).

RVFV-6 binding to Vero E6 cells was further characterized by electron microscopy (FIG. 7B). Cells were incubated with biotinylated RVFV-6 prior to fixing and staining to visualize the biotin bound to the peptide. The peptide forms aggregates on the cell surface and appears to be entering the cell by endocytosis.

Similar to the findings by Schmidt et al., with DENV (Schmidt, Yang et al. 2010), our RVFV peptides apparently bind to the plasma membrane, ideally locating the peptide at the location of virus attachment Like many enveloped viruses, the RVFV genome gains entry to a host cell's cytosol through a pH-dependent fusion of viral and host cell membranes (Filone, Heise et al. 2006). To further examine this, we wanted to determine whether our RVFV peptides also bind to RVFV and if the peptides bind to the RVFV fusion protein Gc following a low pH treatment, such as would be experienced during viral entry through the endocytic pathway.

Figures 8A, 8B:
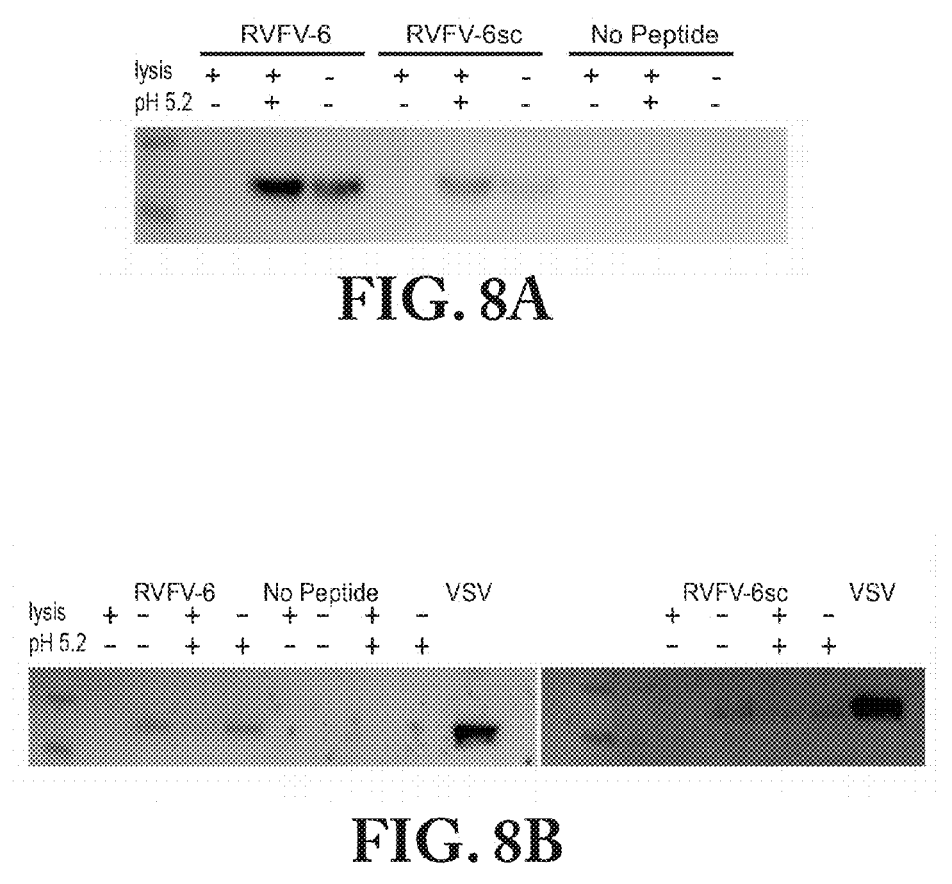

Using RVFV-6 as a representative peptide, we performed immune-precipitation assays using biotinylated peptides bound to streptavidin beads and RVFV-MP12. After washing, bound proteins were resolved by SDS-PAGE and western blots probed with a monoclonal antibody to Gc. When the immune precipitations were carried out at neutral pH, RVFV-6 and to a lesser extent RVFV-6sc, were found to precipitate Gc (FIG. 8A); however, in the presence of the non-ionic detergent, Triton-X, which will solubilize the viral membrane, Gc was not precipitated. These results suggest that RVFV-6 did not bind to Gc directly. In contrast, when the same experiment was performed at low pH (pH 5.2), which is expected to trigger the Gc fusion mechanism, Gc was detected both in the absence and presence of Triton X (FIG. 8A).

Figure 9A:
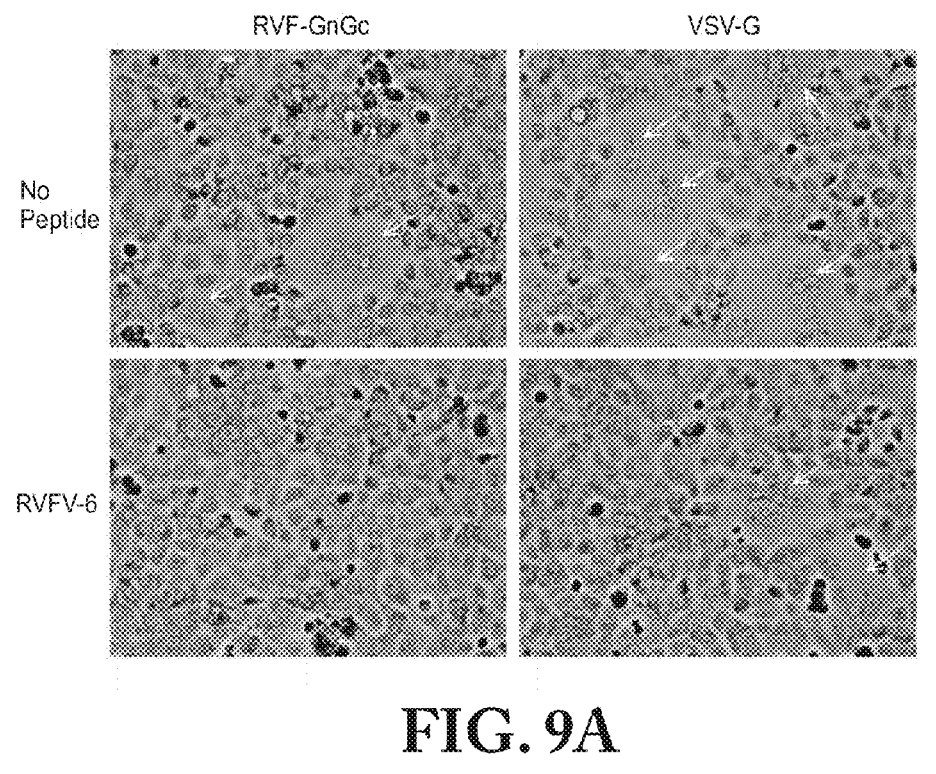
Figure 9B:
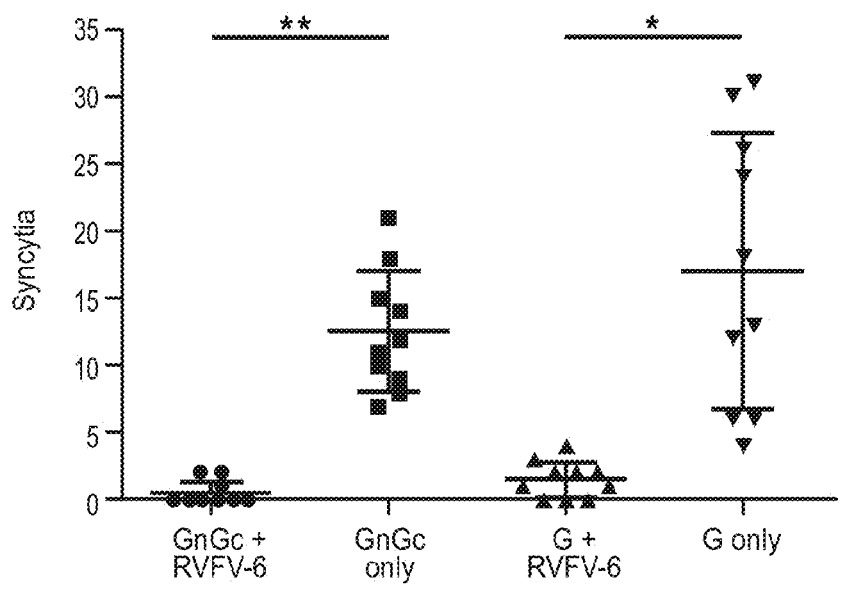

Since our RVFV peptides binds to Gc following low pH-induced conformational changes, we next wanted to determine if the peptides inhibit viral fusion. To assess this, a cell-cell fusion assay was developed for both RVFV and VSV. Vero E6 cells were transfected with a plasmid to express either RVFV-GnGc or VSV-G. When these transfected cells were treated at a low pH, the cells fused together, forming syncytia (FIG. 9). When these cells expressing either RVFV-GnGc or VSV-G were incubated with RVFV-6 and then subjected to low pH, the cell-cell fusion was significantly inhibited for both RVFV ($p<0.0001$) and VSV ($p=0.001$) transfected cells.

By these various tests and those described further below in the Examples, we show the inhibition of RVFV using our new synthetic peptides which are analogous to the RVFV stem of the fusion protein Gc. Our synthetic peptides also inhibit another bunyavirus (ANDY), a filovirus (EBOV), and a rhabdovirus (VSV). Our peptides bind to both RVFV and VSV independent of the fusion protein, and we have shown that peptide binding to the fusion protein only occurs following a low-pH treatment (natural process within the cell), exposing the binding site of the peptide. Virion:cell binding is not inhibited—e.g., the RVFV-6 peptide did not interfere with RVFV or EBOV binding to cells, but the peptide did bind nonspecifically to RVFV independent of the presence of RVFV-Gc. Specific binding to Gc occurred only after a low-pH treatment, which likely exposes the peptide's binding site. Further, we found that peptides inhibit membrane fusion of both RVFV and VSV using a cell:cell fusion assay.

Figure 10B:
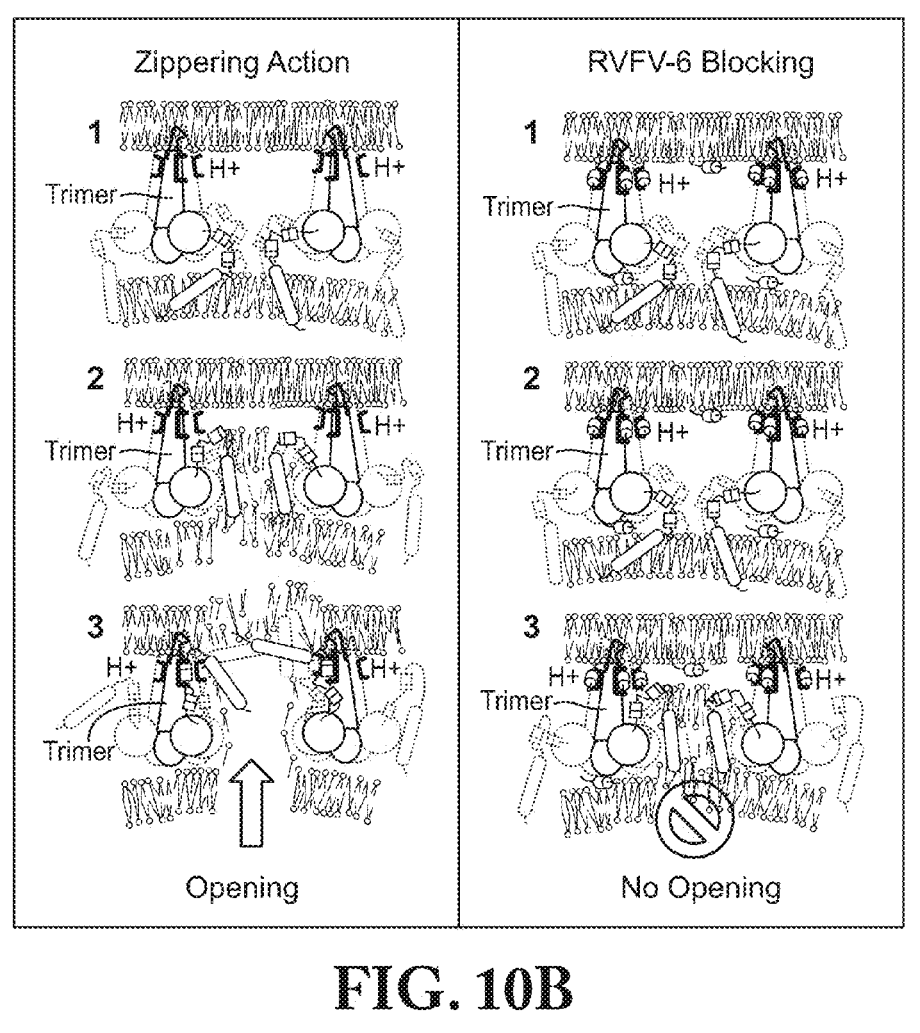
Figure 10C:
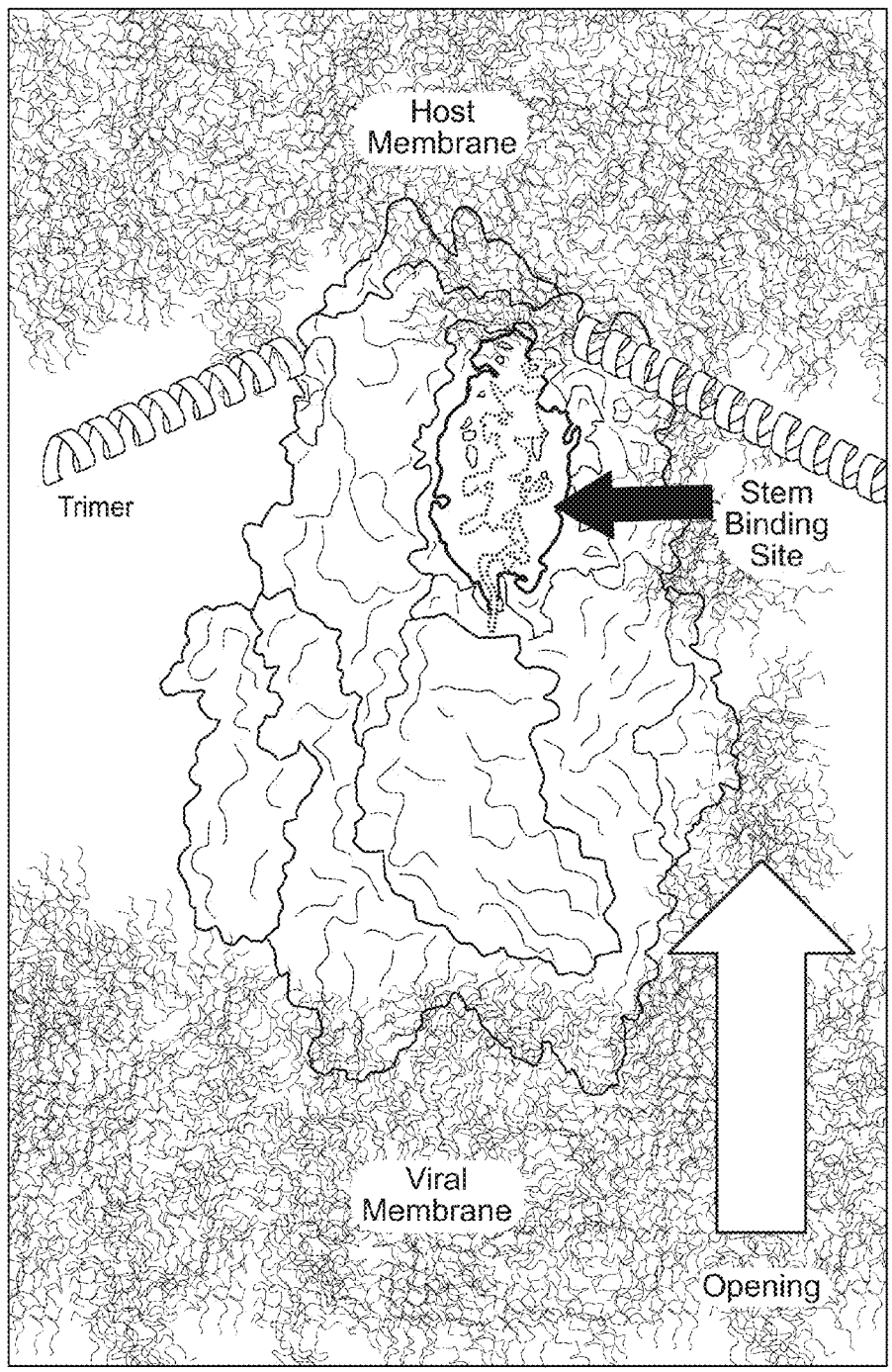
FIG. 10 (A-C) shows a graphical representation of the proposed mechanism of action for these peptides. The initial stages of bunyavirus membrane fusion is shown in Figure A (adapted from (Garry and Garry 2004)). Endocytosis and viral uptake is initiated by virion:cell binding, and conformational rearrangements of Gc in response to acidification initiate glycoprotein rearrangement. This results in insertion of the fusion peptide into the endosomal membrane. The zippering action of the Gc trimers is shown in (Figure B). Here, the Gc stem zips along the fusion protein, bringing the viral and endocytic membranes into close proximity to allow for membrane destabilization and fusion. The RVFV-6 peptide is thought to bind to Gc, preventing this zippering action from occurring, thus blocking fusion. A molecular model of the RVFV Gc trimer complex is shown in (Figure C) with the location of the stem fragments (center portion of stem binding sites) and the stem binding sites indicated. These data were previously published by the inventors (Koehler, Smith et al. 2013).

Although not wishing to be bound by theory, we believe that the proposed mechanism of action is that (1) RVFV-6 binds to the virion and cells, (2) the virus enters into the targeted cell via the endocytic pathway, trafficking the bound peptide into the endocytic pathway, (3) the peptide binds the viral fusion protein following acidification of the endosome and fusion protein rearrangements, and (4) this binding to the fusion protein physically prevents the Gc stem to complete the zippering and fusion process (see FIG. 10).

Our findings are supported by the reports for a stem-based DENV inhibitory peptide, regarding a two-step mechanism of action (Schmidt, Yang et al., 2010). The DENV peptide first binds nonspecifically to the virion membrane and/or cell membrane likely due to hydrophobic interactions of the peptide's amino acids with the membrane. If bound to the cell membrane, the peptide attaches to the virion membrane as it follows through with the second step. In the second step, the virion with bound peptide enters the cell via the endocytic pathway. As the endocytic vesicles are acidified and the pH drops, the viral fusion protein rearranges. These conformational changes exposes an epitope allowing the peptide to bind, preventing complete fusion protein rearrangement and blocking fusion (Schmidt, Yang et al., 2010).

We were surprised at the success of our peptides. Not only did they inhibit RVFV, they inhibited multiple, diverse viruses including an unrelated bunyavirus, a filovirus which uses a class II fusion protein, and a rhabdovirus with a class III fusion protein. These results could be associated with the findings described for the scrambled peptide. Our peptides appear to traffic with the EBOV, ANDY, and/or VSV virion in a similar manner as with RVFV. Post-acidification and fusion protein re-arrangement, our synthetic RVFV peptides could bind the fusion protein, preventing successful fusion.

Our findings suggest that our RVFV peptides enter the endocytic pathway by interacting with the virus independent of a specific interaction with Gc. The peptide subsequently binds to Gc following a triggering of the fusion protein rearrangement initiated by a decrease in pH, resulting in blocking of Gc-mediated fusion. In addition to inhibiting the infectivity of RVFV, our RVFV peptides were found to be broadly active and inhibiting infectivity of multiple viruses.

Due to the small size of our RVFV peptides (approximately 20 amino acids), they would be easy to produce in large quantities using well-known methods, and can be stored, dried, for long periods of time.

In a further embodiment, our peptides can be used in as drug delivery vehicles. Since these peptides (1) bind to the surface of the host cells, (2) traffic through the endocytic pathway, and (3) are toxic to the host cells, they can be used as a drug delivery vehicle if tethered or conjugated to unrelated drugs or therapeutics, taking these to a cell's plasma membrane or the endocytic compartment. In the art currently, there are some compounds that have been targeted to cells. See Ingallinella et al., "Addition of a cholesterol group to an HIV-1 peptide fusion inhibitor dramatically increases its antiviral potency", PNAS, Vol. 106, No. 14, pages 5801-06 (Apr. 7, 2009). This group tethered a peptide inhibitor of HIV to a cholesterol group which targets the peptide to the cell membrane. Also see Rajendran, et al., "Efficient Inhibition of the Alzheimer's Disease B—Secretase by Membrane Targeting", Science, Vol. 320, pates 520-523 (Apr. 25, 2008). In this paper, a potential Alzheimer's peptide therapeutic was targeted to the cell membrane and the endosomal compartment by tethering the peptide to a sterol group.

Our method would entail 1) tethering the therapeutic to the peptide, 2) delivering the drug/peptide, 3) having the drug/peptide bind to a cellular membrane and enter the cell via the endocytic pathway. Our peptide rapidly binds to membranes and is taken up into the cell via the endocytic pathway. Potential drugs could have a site of action on the cell surface (e.g., viral entry inhibitor, a cell receptor agonist or antagonist) or in the endocytic pathway (e.g., viral fusion inhibitor). Drugs and therapeutics that may be tethered/conjugated include, for example, targeted siRNA therapies (ex. siRNAs targeting a viral gene) or enzyme inhibitors (ex. ACE inhibitors) that require entry into a targeted cell. An example of such tethering of a drug to the cholera toxin subunit as described in Snider, C., S. Jayasinghe, K. Hristova, and S. H. White. 2009. MPEx: a tool for exploring membrane proteins. Protein Sci 18:2624-8.

EXAMPLES

Materials and Methods

Identification and Synthesis of Potential Inhibitory Peptides.

RVFV fusion protein Gc amino acid sequence (GenBank P03518) was analyzed for a positive Wimley-White interfacial hydrophobicity score (WWIHS), as previously described (Hrobowski et al., 2005; Sainz et al., 2006) using the program Membrane Protein eXplorer (Snider, 2009). Peptides were generated based on a positive WWIHS and protein domain consideration, and regions selected for peptide generation include Gc domains IIa, IIb, III, and the stem region (Table 1). Control, scrambled peptides (designated with a-sc) were generated by randomly assigning amino acid positions for each amino acid in the experimental peptide. Peptides were synthesized by a solid-phase conventional N-a-9-flurenylmethyloxcarbonyl chemistry and purified by reverse-phase high performance liquid chromatography to greater than 95% (Bio-synthesis, Inc., Lewisville, Tex.). Lyophilized peptides were initially resuspended in 1,1,1,3, 3,3-hexafluoro-2-propanol (Sigma-Aldrich, St. Louis, Mo.), overnight and dried in a vacuum centrifuge. Stock solutions were generated by resuspending all peptides, in 20%-30% dimethyl sulfoxide (DMSO) (Sigma-Aldrich, St. Louis, Mo.) and water (Life Technologies, Grand Island, N.Y.). Peptide concentrations were determined by measuring the absorbance of aromatic amino acid side chains at 280 nm using a Nanodrop (Thermo Scientific, Wilmington, Del.).

Viruses and Cells.

RVFV vaccine strain MP12 (6) and the wild-type pathogenic RVFV-ZHSO1, which was originally isolated from the serum of a fatal human hemorrhagic fever victim in Egypt, during an epidemic in 1977 (25), and ANDV isolate 808034 were used in the assays. These viruses are maintained at the U.S. Army Medical Research Institute of Infectious Diseases (USAMRIID). The green-fluorescent protein (GFP) tagged Zaire ebolavirus, EboZ-eGFP (36), was kindly provided by Dr. Jonathan Towner, Centers for Disease Control and Prevention (Atlanta, Ga.). Pseudotyped viruses RVFV-VSV-luc and VSV-luc were kindly provided by Dr. Robert Doms at the University of Pennsylvania. This pseudotyped virus system is similar to the one developed by Ray et al. (27). Vero E6 cells supplied by USAMRIID's Cell Culture center were maintained in complete medium (cEMEM), Eagle's minimum essential medium (EMEM, Lonza, Basel, Switzerland) supplemented with 10% (v/v) fetal bovine serum (Life Technologies, Grand Island, N.Y.), 100 U/ml penicillin G (Life Technologies, Grand Island, N.Y.), and 100 mg/ml streptomycin (Life Technologies, Grand Island, N.Y.) at 37° C. with 5% $CO_2$.

Virus Inhibition Assays

Working stocks of each peptide were generated by adding stock peptide to cEMEM. For the RVFV and ANDV assays, 6-well plates of confluent Vero E6 cells were infected with 50-75 plaque forming units (pfu) of virus that was pre-incubated with or without peptide in cEMEM for one hour at 37° C. Virus was allowed to adsorb for one hour at 37° C. after which the monolayers were washed once with phosphate buffered saline (PBS, Gibco, Grand Island, N.Y.) and overlaid with EBME (Life Technologies, Grand Island, N.Y.) supplemented with 10% FBS, 1% non-essential amino acids, 4% L-glutamine (Life Technologies, Grand Island, N.Y.), 100 U/ml penicillin G, 100 mg/ml streptomycin, and 1× Fungizone (Life Technologies, Grand Island, N.Y.) containing 0.6% (w/v) SeaKem ME agarose (Lonza, Basel, Switzerland). Cells were incubated at 37° C. with 5% (v/v) $CO_2$ for 3 days (RVFV) or 7 days (ANDV), and a secondary overlay containing EBME supplemented with 10% FBS, 100 U/ml penicillin G, 100 mg/ml streptomycin, 1× Fungizone, and 5% neutral red (Life Technologies, Grand Island, N.Y.) was added. Plaques were subsequently counted over two days starting the following day for RVFV and 3 days following the addition of the secondary overlay for ANDV. For the EboZ-eGFP and pseudotyped infections, signal-optimized concentrations of virus were incubated with a dilution series of peptide, diluted in cEMEM. After a one hour incubation, media was removed from 96-well plates of confluent Vero E6 cells, and virus/peptide was added in triplicate. After a one hour incubation, the inocula were removed, the cells washed once with PBS, and fresh media was added. For EboZ-eGFP, 48 hours post-infection, levels of GFP were measured. For the pseudotyped viruses, luciferase activity was measured the following day using the *Renilla* Luciferase Assay System (Promega, Madison, Wis.).

MTT Toxicity Assay

Peptide toxicity was assessed using the MTT cell proliferation assay (ATCC, Manassas, Va.) according to the manufacturer's instructions. Briefly, Vero E6 cells were incubated with 100 ul cEMEM containing serial dilutions of each peptide for approximately 18 hours prior to the addition of tetrazolium salt (MTT). This salt is reduced in metabolically active cells, forming crystals which are solubilized by detergent. Absorbance was read at 570 nm with a spectrophotometer (Promega/Turner Biosystems, Madison, Wis.)

Peptide-cell Binding Assay

In order to assess peptide binding to cells, a C-terminal biotin conjugated RVFV-6 peptide and a biotin-conjugated RVFV-6 scrambled peptide were synthesized (Bio-synthesis, Inc., Lewisville, Tex.). An immunofluorescence assay was developed to detect peptide binding to Vero E6 cells. Cells were transfected with a plasmid containing a codon-optimized RVFV-ZH548 GnGc expression construct. Cells were incubated with 25 uM peptide in chamber slides for one hour. Cells were then washed extensively with PBS before fixing in 10% buffered formalin for 15 minutes. An anti-biotin antibody conjugated to a Texas Red fluorophore (Abcam, Cambridge, Mass.) was incubated with the cells for one hour. Following washing with PBS, cells were mounted with a DAPI-containing mounting medium (Life Technologies, Grand Island, N.Y.) and observed under a microscope. Images were merged to depict peptide binding (red) and nuclei (blue).

Electron microscopy was conducted to visualize peptide binding to Vero E6 cells treated with and without RVFV-6 peptide. For immunogold labeling, cell monolayers were briefly pre-fixed in 0.2% paraformaldehyde (E.M. Sciences, Warrenton, Pa., USA) at room temperature. After this brief fixation, the cells were washed in PBS and incubated with Goat anti-Biotin 15 nm IgG Gold antibody (Ted Pella, Calif., USA) for two hours at room temperature. Following wash steps, the attached cells were fixed in with 2.5% Glutaraldehyde (E.M. Sciences) and scraped and pelleted by centrifugation. Cell pellets were minced into small pieces, washed in Millonig's Sodium Phosphate Buffer (Tousimis Research, Rockville, Md.), and stored overnight at 4° C. The samples were then post-fixed in 1.0% Osmium Tetroxide (E.M. Sciences), en bloc stained with 2.0% aqueous Uranyl Acetate, dehydrated in a series of graded ethanols, and infiltrated and embedded in DER 736 plastic resin (Tousimis Research). After polymerization for 48 hours at 70° C., blocks from each sample were ultra-thin sectioned using Leica UC7 Ultramicrotome. Thin sections 60 to 80 nanometers in thickness were collected from each sample and mounted onto 300 mesh copper grids. The grids from each sectioned block were then post-stained with Reynold's Lead Citrate and subsequently viewed in a Tecnai Spirit Twin Transmission Electron Microscope, operating at 80 kV.

Peptide-virion Binding Assay

In order to address the mechanics of peptide inhibition of the virus, a binding assay was developed. 25 ul biotin-conjugated RVFV-6 or biotin-conjugated RVFV-6 scrambled peptide was incubated with streptavidin magnetic beads (Life Technologies, Grand Island, N.Y.). Following peptide binding to the beads, unbound peptide was washed away with Tris-buffered saline (TBS, Sigma-Aldrich, St. Louis, Mo.). RVFV-MP12 diluted in cEMEM was added to the beads for one hour at 37° C., allowing for peptide-virion binding. After the one hour, the beads were washed with TBS and treated in one of three conditions: 1) virus bound to beads were lysed using Triton X (Sigma-Aldrich, St. Louis, Mo.), 2) virus bound to the beads were treated with a Earl's salt solution containing 20 mM HEPES and 20 mM MES, pH 5.2 (fusion medium), for 15 minutes to trigger pH-induced glycoprotein rearrangements prior to being lysed, or 3) virus was not pH treated and not lysed. The magnetic beads were washed with TBS (or fusion medium for the pH treated beads) to remove unbound virus, and SDS-PAGE loading buffer (Life Technologies, Grand Island, N.Y.) was added to the beads. Following a 5 minute incubation at 70° C., samples were resolved on a SDS-PAGE gel. The resolved proteins were transferred to a nitrocellulose blot, blocked with 5% Difco (Becton-Dickenson, Franklin Lakes, N.J.) in PBS (block), and incubated with a 1:1000 dilution in block of the mouse anti-RVFV Gc antibody 4D4. Following three washes with PBS containing 0.05% Tween-20 (Sigma-Aldrich, St. Louis, Mo.), a secondary antibody, a horse radish peroxidase conjugated goat anti-mouse antibody (Santa Cruz Biotechnology, Santa Cruz, Calif.) diluted 1:2500 dilution in block), was added for one hour. The blot was washed in PBS containing Tween, and imaged using a camera system (G-box, Syngene, Frederick, Md.).

Virion-cell Binding Assay

A probe-based, real-time RT-PCR assay was used as previously described for RVFV (12) and EBOV (37) to detect the relative amount of virus present in a sample. Two dilutions of RVFV or EboZ-eGFP, $10^4$ and $10^5$ pfu) were pre-treated with 25 uM of each peptide for one hour before infecting a monolayer of Vero E6 cells. One hour post-infection, cells were washed extensively with phosphate buffered saline (PBS) to remove unbound virus, and total RNA was extracted using Trizol (Life Technologies, Grand Island, N.Y.) according to the manufacturer's instructions. Equal amounts of RNA were used in the real-time RT-PCR assay as previously described using the Power SYBR Green RNA-to-Ct 1-Step Kit (Applied Biosystems/Life Technologies, Grand Island, N.Y.) on a Bio-Rad CFX96 real-time instrument (Bio-Rad, Hercules, Calif.).

Cell-cell Fusion Assay

A plasmid-based cell-cell fusion assay was developed similar to what was described previously using alphavirus replicon vectors (13) to assess if RVFV-6 inhibits the fusion process. Codon-optimized RVFV strain ZH548 as well as codon-optimized T7 polymerase was previously cloned into the mammalian dual-expression vector pBud-CE4.1 (Life Technologies, Grand Island, N.Y.) to create the plasmid pBud-CE4.1-RVFV548-GnGc-T7-opti. Vero E6 cells in a 6-well plate were transfected using Fugene HD Transfection Reagent (Promega, Madison, Wis.) with pBud-CE4.1-RVFV548-GnGc-T7-opti or a mammalian expression plasmid containing a VSV-G expression cassette, kindly provided by Dr. Robert Doms. Approximately 18 hours later, the transfected cells were harvested and seeded onto wells of an 8-well chamber slide (Lab-Tek II chamber slide RS, Thermo Scientific, Wilmington, Del.). The cells transfected with pBud-CE4.1-RVFV548-GnGc-T7-opti were seeded at $1 \times 10^5$ cells/well. Cells transfected with VSV-G were seeded at $1.25 \times 10^4$ cells/well, and untransfected cells were added to bring the final concentration to $1 \times 10^5$ cells/well. Twenty-four hours later, the media was exchanged with cEMEM with or without diluted peptide. Following a one hour incubation at 37° C., the cells were treated with the low pH fusion medium. EMEM, which is at a higher pH, is buffered and has a red color at neutral pH and yellow at an acidic pH, was added to the wells to raise the pH, as indicated by the red color, and the slides were incubated at 37° C. with 5% $CO_2$. Five hours later, cells were fixed for 7 minutes with ice-cold methanol and air dried. Cells were stained for 15 minutes with a 1:10 dilution of Giemsa stain (Promega, Madison, Wis.) in water. Slides were air dried, mounted with a DAPI-containing mounting medium, and were observed under a microscope. Statistical significance comparing the number of fusion events with and without peptide treatment was assessed by a paired, two-tailed t-test using Prism 5 (GraphPad Software, La Jolla, Calif.).

While particular embodiments of the present invention have been shown and described, it will be obvious to those skilled in the art that changes and modifications may be made without departing from this invention. Therefore, it is intended that the claims herein are to include all such obvious changes and modifications as fall within the true spirit and scope of this invention.

REFERENCES

1. Adam, A. A., M. S. Karsany, and I. Adam. 2009. Manifestations of severe Rift Valley fever in Sudan. Int J Infect Dis 14:e179-80.
2. Allison, S. L., J. Schalich, K. Stiasny, C. W. Mandl, and F. X. Heinz. 2001. Mutational evidence for an internal fusion peptide in flavivirus envelope protein E. J Virol 75:4268-75.
3. Allison, S. L., J. Schalich, K. Stiasny, C. W. Mandl, C. Kunz, and F. X. Heinz. 1995. Oligomeric rearrangement of tick-borne encephalitis virus envelope proteins induced by an acidic pH. J Virol 69:695-700.
4. Borio, L., T. Inglesby, C. J. Peters, A. L. Schmaljohn, J. M. Hughes, P. B. Jahrling, T. Ksiazek, K. M. Johnson, A. Meyerhoff, T. O'Toole, M. S. Ascher, J. Bartlett, J. G. Breman, E. M. Eitzen, Jr., M. Hamburg, J. Hauer, D. A. Henderson, R. T. Johnson, G. Kwik, M. Layton, S. Lillibridge, G. J. Nabel, M. T. Osterholm, T. M. Perl, P. Russell, and K. Tonat. 2002. Hemorrhagic fever viruses as biological weapons: medical and public health management. JAMA 287:2391-405.
5. Bressanelli, S., K. Stiasny, S. L. Allison, E. A. Stura, S. Duquerroy, J. Lescar, F. X. Heinz, and F. A. Rey. 2004. Structure of a flavivirus envelope glycoprotein in its low-pH-induced membrane fusion conformation. EMBO J 23:728-38.
6. Caplen, H., C. J. Peters, and D. H. Bishop. 1985. Mutagen-directed attenuation of Rift Valley fever virus as a method for vaccine development. J Gen Virol 66 (Pt 10):2271-7.
7. Colotto, A., and R. M. Epand. 1997. Structural study of the relationship between the rate of membrane fusion and the ability of the fusion peptide of influenza virus to perturb bilayers. Biochemistry 36:7644-51.
8. Costin, J. M., E. Jenwitheesuk, S. M. Lok, E. Hunsperger, K. A. Conrads, K. A. Fontaine, C. R. Rees, M. G. Rossmann, S. Isern, R. Samudrala, and S. F. Michael. Structural optimization and de novo design of dengue virus entry inhibitory peptides. PLoS Negl Trop Dis 4:e721.
9. Costin, J. M., E. Jenwitheesuk, S. M. Lok, E. Hunsperger, K. A. Conrads, K. A. Fontaine, C. R. Rees, M. G. Rossmann, S. Isern, R. Samudrala, and S. F. Michael. 2010. Structural optimization and de novo design of dengue virus entry inhibitory peptides. PLoS Negl Trop Dis 4:e721.
10. Daubney, R., J. Hudson, and P. Garnham. 1931. Enzootic hepatitis or Rift Valley fever. An undescribed virus disease of sheep, cattle and man from East Africa. J. Path. Bact 34:545-579.
11. Digoutte, J. P., and C. J. Peters. 1989. General aspects of the 1987 Rift Valley fever epidemic in Mauritania. Res Virol 140:27-30.
12. Drosten, C., S. Gottig, S. Schilling, M. Asper, M. Panning, H. Schmitz, and S. Gunther. 2002. Rapid detection and quantification of RNA of Ebola and Marburg viruses, Lassa virus, Crimean-Congo hemorrhagic fever virus, Rift Valley fever virus, dengue virus, and yellow fever virus by real-time reverse transcription-PCR. J Clin Microbiol 40:2323-30.
13. Durand, J. P., M. Bouloy, L. Richecoeur, C. N. Peyrefitte, and H. Tolou. 2003. Rift Valley fever virus infection among French troops in Chad. Emerg Infect Dis 9:751-2.

14. Filone, C. M., M. Heise, R. W. Doms, and A. Bertolotti-Ciarlet. 2006. Development and characterization of a Rift Valley fever virus cell-cell fusion assay using alphavirus replicon vectors. Virology 356:155-64.
15. Gallaher, W. R. 1987. Detection of a fusion peptide sequence in the transmembrane protein of human immunodeficiency virus. Cell 50:327-8.
16. Gallaher, W. R., J. M. Ball, R. F. Garry, M. C. Griffin, and R. C. Montelaro. 1989. A general model for the transmembrane proteins of HIV and other retroviruses. AIDS Res Hum Retroviruses 5:431-40.
17. Garry, C. E., and R. F. Garry. 2004. Proteomics computational analyses suggest that the carboxyl terminal glycoproteins of Bunyaviruses are class II viral fusion protein (beta-penetrenes). Theor Biol Med Model 1:10.
18. Harrison, S. C. 2008. Viral membrane fusion. Nat Struct Mol Biol 15:690-8.
19. Hrobowski, Y. M., R. F. Garry, and S. F. Michael. 2005. Peptide inhibitors of dengue virus and West Nile virus infectivity. Virol J 2:49.
20. Johnson, K. M., J. E. Vogel, and P. H. Peralta. 1966. Clinical and serological response to laboratory-acquired human infection by Indiana type vesicular stomatitis virus (VSV). Am J Trop Med Hyg 15:244-6.
21. Kilby, J. M., S. Hopkins, T. M. Venetta, B. DiMassimo, G. A. Cloud, J. Y. Lee, L. Alldredge, E. Hunter, D. Lambert, D. Bolognesi, T. Matthews, M. R. Johnson, M. A. Nowak, G. M. Shaw, and M. S. Saag. 1998. Potent suppression of HIV-1 replication in humans by T-20, a peptide inhibitor of gp41-mediated virus entry. Nat Med 4:1302-7.
22. Kilgore, N. R., K. Salzwedel, M. Reddick, G. P. Allaway, and C. T. Wild. 2003. Direct evidence that C-peptide inhibitors of human immunodeficiency virus type 1 entry bind to the gp41 N-helical domain in receptor-activated viral envelope. J Virol 77:7669-72.
23. Madani, T. A., Y. Y. Al-Mazrou, M. H. Al-Jeffri, A. A. Mishkhas, A. M. Al-Rabeah, A. M. Turkistani, M. O. Al-Sayed, A. A. Abodahish, A. S. Khan, T. G. Ksiazek, and O. Shobokshi. 2003. Rift Valley fever epidemic in Saudi Arabia: epidemiological, clinical, and laboratory characteristics. Clin Infect Dis 37:1084-92.
24. Malashkevich, V. N., B. J. Schneider, M. L. McNally, M. A. Milhollen, J. X. Pang, and P. S. Kim. 1999. Core structure of the envelope glycoprotein GP2 from Ebola virus at 1.9-A resolution. Proc Natl Acad Sci USA 96:2662-7.
25. Meegan, J. M., H. Hoogstraal, and M. I. Moussa. 1979. An epizootic of Rift Valley fever in Egypt in 1977. Vet Rec 105:124-5.
26. Modis, Y., S. Ogata, D. Clements, and S. C. Harrison. 2004. Structure of the dengue virus envelope protein after membrane fusion. Nature 427:313-9.
27. Ray, N., J. Whidby, S. Stewart, J. W. Hooper, and A. Bertolotti-Ciarlet. 2009. Study of Andes virus entry and neutralization using a pseudovirion system. J Virol Methods 163:416-23.
28. Rey, F. A., F. X. Heinz, C. Mandl, C. Kunz, and S. C. Harrison. 1995. The envelope glycoprotein from tick-borne encephalitis virus at 2 A resolution. Nature 375:291-8.
29. Roche, S., S. Bressanelli, F. A. Rey, and Y. Gaudin. 2006. Crystal structure of the low-pH form of the vesicular stomatitis virus glycoprotein G. Science 313:187-91.
30. Roche, S., F. A. Rey, Y. Gaudin, and S. Bressanelli. 2007. Structure of the prefusion form of the vesicular stomatitis virus glycoprotein G. Science 315:843-8.
31. Sainz, B., Jr., E. C. Mossel, W. R. Gallaher, W. C. Wimley, C. J. Peters, R. B. Wilson, and R. F. Garry. 2006. Inhibition of severe acute respiratory syndrome-associated coronavirus (SARS-CoV) infectivity by peptides analogous to the viral spike protein. Virus Res 120:146-55.
32. Schmidt, A. G., P. L. Yang, and S. C. Harrison. 2010. Peptide inhibitors of dengue-virus entry target a late-stage fusion intermediate. PLoS Pathog 6:e1000851.
33. Shoemaker, T., C. Boulianne, M. J. Vincent, L. Pezzanite, M. M. Al-Qahtani, Y. Al-Mazrou, A. S. Khan, P. E. Rollin, R. Swanepoel, T. G. Ksiazek, and S. T. Nichol. 2002. Genetic analysis of viruses associated with emergence of Rift Valley fever in Saudi Arabia and Yemen, 2000-01. Emerg Infect Dis 8:1415-20.
34. Snider, C., S. Jayasinghe, K. Hristova, and S. H. White. 2009. MPEx: a tool for exploring membrane proteins. Protein Sci 18:2624-8.
35. Tischler, N. D., A. Gonzalez, T. Perez-Acle, M. Rosemblatt, and P. D. Valenzuela. 2005. Hantavirus Gc glycoprotein: evidence for a class II fusion protein. J Gen Virol 86:2937-47.
36. Towner, J. S., J. Paragas, J. E. Dover, M. Gupta, C. S. Goldsmith, J. W. Huggins, and S. T. Nichol. 2005. Generation of eGFP expressing recombinant Zaire ebolavirus for analysis of early pathogenesis events and high-throughput antiviral drug screening. Virology 332:20-7.
37. Trombley, A. R., L. Wachter, J. Garrison, V. A. Buckley-Beason, J. Jahrling, L. E. Hensley, R. J. Schoepp, D. A. Norwood, A. Goba, J. N. Fair, and D. A. Kulesh. 2010. Comprehensive panel of real-time TaqMan polymerase chain reaction assays for detection and absolute quantification of filoviruses, arenaviruses, and New World hantaviruses. Am J Trop Med Hyg 82:954-60.
38. Weissenhorn, W., A. Carfi, K. H. Lee, J. J. Skehel, and D. C. Wiley. 1998. Crystal structure of the Ebola virus membrane fusion subunit, GP2, from the envelope glycoprotein ectodomain. Mol Cell 2:605-16.
39. Wild, C., T. Greenwell, and T. Matthews. 1993. A synthetic peptide from HIV-1 gp41 is a potent inhibitor of virus-mediated cell-cell fusion. AIDS Res Hum Retroviruses 9:1051-3.
40. Wilson, I. A., J. J. Skehel, and D. C. Wiley. 1981. Structure of the haemagglutinin membrane glycoprotein of influenza virus at 3 A resolution. Nature 289:366-73.
41. Ashkenazi A, Shai Y (2011) Insights into the mechanism of HIV-1 envelope induced membrane fusion as revealed by its inhibitory peptides. Eur Biophys J. 42. Schmidt A G, Lee K, Yang P L, Harrison S C (2012) Small-molecule inhibitors of dengue-virus entry. PLoS Pathog 8: e1002627.
43. Vialat P, Muller R, Vu T H, Prehaud C, Bouloy M (1997) Mapping of the mutations present in the genome of the Rift Valley fever virus attenuated MP12 strain and their putative role in attenuation. Virus Res 52: 43-50.
44. Spik K, Shurtleff A, McElroy A K, Guttieri M C, Hooper J W, et al. (2006) Immunogenicity of combination DNA vaccines for Rift Valley fever virus, tick-borne encephalitis virus, Hantaan virus, and Crimean Congo hemorrhagic fever virus. Vaccine 24: 4657-4666.
45. Ramanathan H N, Jonsson C B (2008) New and Old World hantaviruses differentially utilize host cytoskeletal components during their life cycles.

46. Koehler J W, Dupuy L C, Garrison A R, Beitzel B F, Richards M J, et al. (2011) Novel plant-derived recombinant human interferons with broad spectrum antiviral activity. Antiviral Res 92: 461-469.
47. Battles J K, Dalrymple J M (1988) Genetic variation among geographic isolates of Rift Valley fever virus. Am J Trop Med Hyg 39: 617-631.
48. Ingallinella et al., "Addition of a cholesterol group to an HIV-1 peptide fusion inhibitor dramatically increases its antiviral potency", PNAS, Vol. 106, No. 14, pages 5801-06 (Apr. 7, 2009).
49. Rajendran, et al., "Efficient Inhibition of the Alzheimer's Disease B-Secretase by Membrane Targeting", Science, Vol. 320, pates 520-523
50. Shukla, A et al., 2010. M-cell targeted delivery of recombinant hepatitis B surface antigen using cholera toxin B subunit conjugated bilosomes. International Journal of Pharmaceutics. 385:47-52.

The teachings of the references cited herein and throughout the patent application herein are incorporated by reference herein in their entirety.

We claim:

1. A method of inhibiting the fusion of RVFV, vesicular stomatitis virus (VSV), and/or Ebola virus (EBOV) to a target cell, comprising the steps of
   a) exposing a peptide to a virion of RVFV, VSV and/or EBOV under conditions that the peptide binds to the virion,
   wherein the peptide is an antiviral RVFV peptide having the amino acid sequence selected from the group consisting of
   WNFFDWFSGLMSWFGGPLKLY (SEQ ID NO:5), designated RVFV-5,
   WNFFDWFSGLMSWFGGPLK (SEQ ID NO:6), designated RVFV-6,
   WNFFDWFSGLMSWFGGPLKTI (SEQ ID NO:7), designated RVFV-7,
   SWNFFDWFSGLMSWFGGPLK (SEQ ID NO:8), designated RVFV-8,
   SGSWNFFDWFSGLMSWFGG (SEQ ID NO:9), designated RVFV-9, and
   SGSWNFFDWFSGLMSWFGGPL (SEQ ID NO:10) designated RVFV-10 and
   b) allowing the virion bound with the peptide to enter the target cell and bind to a viral fusion protein, so that the viral fusion protein does not fuse a viral membrane with a cellular membrane.

2. The method of claim 1, wherein the peptide has the amino acid sequence of WNFFDWFSGLMSWFGGPLK (SEQ ID NO:6) or SGSWNFFDWFSGLMSWFGGPL (SEQ ID NO:10).

3. The method of claim 1, wherein the peptide is suspended in a pharmaceutically acceptable carrier.

4. A method for treating or inhibiting post-exposure infection in a mammal by RVFV VSV and/or EBOV, by inhibiting fusion of RVFV, VSV, and/or EBOV to a target cell within the mammal, comprising the step of:
   administering to a mammal that has been exposed or will be exposed to RVFV, VSV and/or EBOV an antiviral composition comprising an RVFV peptide having the amino acid sequence selected from the group consisting of WNFFDWFSGLMSWFGGPLKLY (SEQ ID NO:5), designated RVFV-5,
WNFFDWFSGLMSWFGGPLK (SEQ ID NO:6), designated RVFV-6,
WNFFDWFSGLMSWFGGPLKTI (SEQ ID NO:7), designated RVFV-7,
SWNFFDWFSGLMSWFGGPLK (SEQ ID NO:8), designated RVFV-8,
SGSWNFFDWFSGLMSWFGG (SEQ ID NO:9), designated RVFV-9, and
SGSWNFFDWFSGLMSWFGGPL (SEQ ID NO:10) designated RVFV-10, suspended in a pharmaceutically acceptable carrier, under conditions such that the RVFV peptide binds to a virion of RVFV, VSV and/or EBOV, and the virion bound with the RVFV peptide enters the target cell within the mammal and bind to a viral fusion protein, so that the viral fusion protein does not fuse a viral membrane with a cellular membrane, thereby inhibiting fusion and effecting treatment or inhibition of post-exposure infection.

5. The method of claim 4, wherein the mammal is a human.

6. The method of claim 4, wherein the composition is administered intravenously, intramuscularly, or subcutaneously.

7. The method of claim 4, wherein the peptide is suspended in solution of DMSO and water.

8. The method of claim 4, wherein the peptide has the amino acid sequence of WNFFDWFSGLMSWFGGPLK (SEQ ID NO:6) or SGSWNFFDWFSGLMSWFGGPL (SEQ ID NO:10).

* * * * *

SEQUENCE LISTING

```
<160> NUMBER OF SEQ ID NOS: 12

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Tyr Trp Thr Gly Ser Ile Ser Pro Lys Cys Leu Ser Ser Arg Arg Cys
1               5                   10                  15

His Leu Val

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Gly Cys Gly Cys Phe Asn Val Asn Pro Ser Cys Leu Phe Val His
1               5                   10                  15

Thr Tyr Leu

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Gly Ala Ser Ser Ser Arg Phe Thr Asn Trp Gly Ser Val Ser Leu
1               5                   10                  15

Ser Leu Asp

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Phe Val Gly Ala Ala Val Ser Cys Asp Ala Ala Phe Leu Asn Leu Thr
1               5                   10                  15

Gly Cys Tyr
```

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Asn Phe Phe Asp Trp Phe Ser Gly Leu Met Ser Trp Phe Gly Gly
1               5                   10                  15

Pro Leu Lys Leu Tyr
            20

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Trp Asn Phe Phe Asp Trp Phe Ser Gly Leu Met Ser Trp Phe Gly Gly
1               5                   10                  15

Pro Leu Lys

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Trp Asn Phe Phe Asp Trp Phe Ser Gly Leu Met Ser Trp Phe Gly Gly
1               5                   10                  15

Pro Leu Lys Thr Ile
            20

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Trp Asn Phe Phe Asp Trp Phe Ser Gly Leu Met Ser Trp Phe Gly
1               5                   10                  15

Gly Pro Leu Lys
            20

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

```
Ser Gly Ser Trp Asn Phe Phe Asp Trp Phe Ser Gly Leu Met Ser Trp
1               5                   10                  15

Phe Gly Gly

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Gly Ser Trp Asn Phe Phe Asp Trp Phe Ser Gly Leu Met Ser Trp
1               5                   10                  15

Phe Gly Gly Pro Leu
            20

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met Phe Leu Gly Trp Ser Phe Asp Phe Gly Ser Leu Trp Gly Asn Lys
1               5                   10                  15

Pro Trp Phe

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Trp Ser Ser Gly Leu Pro Phe Gly Asn Phe Gly Leu Ser Trp Phe Asp
1               5                   10                  15

Met Gly Phe Trp Ser
            20
```